(12) United States Patent
Sugiura et al.

(10) Patent No.: US 11,584,907 B2
(45) Date of Patent: Feb. 21, 2023

(54) CELL CULTURE APPARATUS AND CELL CULTURE METHOD

(71) Applicant: NATIONAL INSTITUTE OF ADVANCED INDUSTRIAL SCIENCE AND TECHNOLOGY, Tokyo (JP)

(72) Inventors: Shinji Sugiura, Tsukuba (JP); Taku Satoh, Tsukuba (JP); Reiko Nagasaki, Tsukuba (JP); Toshiyuki Kanamori, Tsukuba (JP)

(73) Assignee: NATIONAL INSTITUTE OF ADVANCED INDUSTRIAL SCIENCE AND TECHNOLOGY

( * ) Notice: Subject to any disclaimer, the term of this patent is extended or adjusted under 35 U.S.C. 154(b) by 142 days.

(21) Appl. No.: 16/646,183

(22) PCT Filed: Sep. 7, 2018

(86) PCT No.: PCT/JP2018/033183
§ 371 (c)(1),
(2) Date: Mar. 11, 2020

(87) PCT Pub. No.: WO2019/054288
PCT Pub. Date: Mar. 21, 2019

(65) Prior Publication Data
US 2020/0277557 A1 Sep. 3, 2020

(30) Foreign Application Priority Data

Sep. 13, 2017 (JP) .............................. JP2017-176137

(51) Int. Cl.
*C12M 3/00* (2006.01)
*C12M 1/00* (2006.01)
(Continued)

(52) U.S. Cl.
CPC .............. *C12M 23/34* (2013.01); *C12M 3/00* (2013.01); *C12M 25/02* (2013.01); *C12M 29/10* (2013.01);
(Continued)

(58) Field of Classification Search
CPC ...... C12M 23/34; C12M 25/02; C12M 29/10; C12M 29/14; C12M 29/18; C12M 3/00;
(Continued)

(56) References Cited

U.S. PATENT DOCUMENTS

| 2007/0217964 A1* | 9/2007 | Johnson | ................. C12M 35/04 422/130 |
| 2015/0111240 A1* | 4/2015 | Wamhoff | ............. C12N 5/0697 435/29 |

(Continued)

FOREIGN PATENT DOCUMENTS

| JP | 2007-202499 A | 8/2007 |
| JP | 2016-535591 A | 11/2016 |

(Continued)

OTHER PUBLICATIONS

International Search Report dated Dec. 4, 2018 in corresponding PCT International Application No. PCT/JP2018/033183.

(Continued)

*Primary Examiner* — Lydia Edwards
(74) *Attorney, Agent, or Firm* — Ostrolenk Faber LLP

(57) ABSTRACT

A cell culture apparatus is provided, including a storage tank including one or a plurality of cell culture units, in which the cell culture unit includes a culture chamber having an inner surface-side space in which a culture solution is stored, a permeable membrane having a first surface to which cells are adherable and a second surface opposite to the first surface, the first surface facing the inner surface-side space, a culture solution storage chamber that stores the culture (Continued)

solution, a culture solution introduction flow path that introduces the culture solution in the culture solution storage chamber to the inner surface-side space, and a culture solution discharge flow path that sends, to the culture solution storage chamber, the culture solution which permeates through the membrane from the inner surface-side space and flows into an outer surface-side space that the second surface of the membrane faces.

8 Claims, 15 Drawing Sheets

(51) Int. Cl.
   *C12M 1/02* (2006.01)
   *C12M 1/12* (2006.01)
   *C12N 5/071* (2010.01)

(52) U.S. Cl.
   CPC ............ *C12N 5/067* (2013.01); *C12N 5/069* (2013.01); *C12N 2513/00* (2013.01)

(58) Field of Classification Search
   CPC .... C12M 41/14; C12N 2513/00; C12N 5/067; C12N 5/069
   See application file for complete search history.

(56) References Cited

U.S. PATENT DOCUMENTS

| | | |
|---|---|---|
| 2016/0168601 A1 | 6/2016 | Mimitsuka |
| 2017/0158997 A1 | 6/2017 | Ingber et al. |
| 2018/0112171 A1 | 4/2018 | Asai |

FOREIGN PATENT DOCUMENTS

| | | |
|---|---|---|
| JP | 2017-079633 A | 5/2017 |
| JP | 2018-064519 A | 4/2018 |
| WO | WO 2010/038613 A1 | 4/2010 |
| WO | WO 2015/004482 A2 | 1/2015 |
| WO | WO 2015/061372 A1 | 4/2015 |
| WO | WO 2016/158233 A1 | 10/2016 |
| WO | WO 2017/154880 A1 | 9/2017 |
| WO | WO 2017/154899 A1 | 9/2017 |

OTHER PUBLICATIONS

Written Opinion dated Dec. 4, 2018 in corresponding PCT International Application No. PCT/JP2018/033183.
J.W. Scannell et al., "Diagnosing the decline in pharmaceutical R&D efficiency," Nat. Rev. Drug Discov., 11:191-200 (2012).
F. Pammolli et al., "The productivity crisis in pharmaceutical R&D," Nat. Rev. Drug Discov., 10:428-438 (2011).
P.M. van Midwoud et al., "Microfluidic devices for in vitro studies on liver drug metabolism and toxicity," Integr. Biol., 3:509-521 (2011).
A.M. Ghaemmaghami et al., "Biomimetic tissues on a chip for drug discovery," Drug Discov. Today, 17:173-181 (2012).
S.N. Bhatia et al., "Microfluidic organs-on-chips," Nat. Biotechnol., 32:760-772 (2014).
M. Baker, "A Living System On a Chip," Nature, 471:661-665 (2011).
J.H. Sung et al., "Microfabricated mammalian organ systems and their integration into models of whole animals and humans," Lab Chip, 13:1201-1212 (2013).
K. Domansky et al., "Perfused multiwell plate for 3D liver tissue engineering," Lab Chip, 10:51-58 (2010).
T. Takebe et al., Vascularized and functional human liver from an iPSC-derived organ bud transplant, Nature., 499(7459):481-485 (2013).
F.M. White, "Viscous Fluid Flow," McGraw-Hill Companies, Inc., Boston, pp. 106-108 and 112-113, 2006.
Y. Imura et al., "Micro Total Bioassay System for Ingested Substances: Assessment of Intestinal Absorption, Hepatic Metabolism, and Bioactivity," Anal Chem, 82:9983-9988 (2010).
K. Rennert et al., "A microfluidically perfused three dimensional human liver model," Biomaterials, 71:119-131 (2015).

* cited by examiner

CELL CULTURE APPARATUS AND CELL CULTURE METHOD

CROSS-REFERENCE TO RELATED APPLICATIONS

The present application is a 35 U.S.C. §§ 371 national phase conversion of PCT International Application No. PCT/JP2018/033183, filed Sep. 7, 2018, which claims priority to Japanese Patent Application No. 2017-176137, filed Sep. 13, 2017, the contents of which are incorporated herein by reference. The PCT International Application was published in the Japanese language.

TECHNICAL FIELD

The present invention relates to a cell culture apparatus and a cell culture method.

BACKGROUND ART

In recent years, development costs for pharmaceutical drugs have increased exponentially (for example, see NPL 1), and the success rate of clinical trials has decreased year by year (for example, see NPL 2). One reason for this is that results of animal experiments cannot be directly applied to clinical trials due to species differences between animals and humans. In addition, in development of chemical products such as cosmetics, in some cases, it is difficult to use experimental animals, especially in Europe. Under such circumstances, there are increasing expectations for in vitro cell assays in which human-derived cultured cells are used.

On the other hand, monolayer culture used in cell assays in the related art is often problematic in that the environment surrounding the cells is greatly different from the in vivo environment, and many functions expressed in the body are lost in cultured cells. Advances in a micro-processing technique or a three-dimensional culture technique in recent years are expected to overcome the problem of losing many functions expressed in the body in cultured cells and simultaneously improve throughput and reliability of cell assays (for example, see NPL 3 and NPL 4). In particular, the concept of organ-on-a-chip, which handles a microfluidic device that reproduces a physiological three-dimensional culture environment in vitro as an organ, has expanded, and research considering application to development of pharmaceutical drugs is being globally developed (for example, see NPL 5 and NPL 6). Furthermore, the concept of body-on-a-chip, which aims to reproduce an individual response by connecting a plurality of organ models reconstructed in vitro with each other through micro-flow paths or the like has also been proposed and has been rapidly attracting attention (for example, see NPL 7).

As described above, a cell culture apparatus that reconstructs an organ model formed of human-derived cultured cells in vitro and reproduces physiological functions is expected to improve the reliability of cell assays. For example, since the liver is a major organ involved in drug metabolism in the living body, expectations for a culture technique of a three-dimensional liver tissue are particularly high. In order to evaluate drug metabolism using three-dimensional liver tissue, the liver function has to be maintained for a long time in vitro. For this reason, it is necessary to construct a three-dimensional tissue having a vascular network, but a method for constructing a three-dimensional tissue having a vascular network in vitro has not as yet been established. Therefore, constructing a three-dimensional tissue having a vascular network in vitro has become a major challenge.

In NPL 8 and PTL 1, an apparatus for perfusion culture of a three-dimensional tissue by disposing cells on a membrane and feeding a culture solution to the membrane using an external peristaltic pump or a built-in peristaltic pump has been reported.

CITATION LIST

Patent Literature

[PTL 1] Japanese Unexamined Patent Application, First Publication No. 2017-79633

Non-Patent Literature

[NPL 1] Scannell, J. W. et al. Nat. Rev. Drug Discov., 11, 191 (2012)
[NPL 2] Pammolli, F. et al. Nat. Rev. Drug Discov., 10, 428 (2011)
[NPL 3] van Midwoud, P. M. et al. Integr. Biol., 3, 509 (2012)
[NPL 4] Ghaemmaghami, A. M. et al. Drug Discov. Today, 17, 173 (2012)
[NPL 5] Bhatia, S. N. et al. Nat. Biotechnol., 32, 760 (2014)
[NPL 6] Baker, M. Nature, 471, 661 (2011)
[NPL 7] Sung, J. H. et al. Lab Chip, 13, 1201 (2013)
[NPL 8] Domansky, K. et al. Lab Chip, 10, 51 (2010)
[NPL 9] Takebe, T. et al. Nature, 499(7459): 481 (2013)

DISCLOSURE OF INVENTION

Technical Problem

An example has been reported in which a vascular network-deployed liver tissue produced by co-culturing hepatocytes and vascular endothelial cells is transplanted into a living body and correctly attached (see NPL 9).

However, it has been difficult for the culture apparatus to sufficiently reproduce a three-dimensional tissue formed in the living body. For example, in the culture apparatus, formation of the vascular tissue in a three-dimensional tissue in a system in which hepatocytes and vascular endothelial cells are co-cultured has not been reported. Therefore, it is considered that maintenance of the liver function for a long time is difficult (for example, see NPL 8).

An object of the present invention is to provide a cell culture apparatus and a cell culture method that can construct a three-dimensional tissue that can reproduce physiological functions in vivo.

Solution to Problem

According to a first aspect of the present invention, a cell culture apparatus is provided, including: a storage tank having one or a plurality of cell culture units, in which the cell culture unit includes a culture chamber having an inner surface-side space in which a culture solution is stored, a permeable membrane having a first surface to which cells are adherable and a second surface opposite to the first surface, the first surface facing the inner surface-side space, a culture solution storage chamber that stores the culture solution, a culture solution introduction flow path that introduces the culture solution in the culture solution storage chamber to the inner surface-side space, and a culture solution discharge flow path that sends, to the culture solution storage chamber, the culture solution which permeates through the membrane from the inner surface-side space and flows into an outer surface-side space that the second surface of the membrane faces.

A backflow prevention mechanism may be further provided that regulates a flow of the culture solution reverse to a circulation flow of the culture solution returning back to the culture solution storage chamber from the culture solution storage chamber via the inner surface-side space and the outer surface-side space.

The backflow prevention mechanism may be provided in the culture solution introduction flow path.

The backflow prevention mechanism may be a Laplace valve that prevents gas flow in a direction reverse to the circulation flow, the Laplace valve may be provided in the culture solution introduction flow path, and an extension pipeline connected to the culture solution introduction flow path may be provided in the culture chamber.

A bypass flow path that introduces the culture solution in the inner surface-side space to the culture solution discharge flow path may be further provided without passing through the membrane.

The bypass flow path may have a resistance flow path part of which a flow path sectional area is 1/10 or less of that of the other part in the bypass flow path.

The storage tank may have the plurality of cell culture units, and at least two of the culture chambers in the plurality of cell culture units or at least two of second culture solution storage chambers in the plurality of cell culture units may communicate with each other so that gas is allowed to flow therethrough.

The culture chamber and the culture solution storage chamber may have vent holes through which gas is supplied to and discharged from the culture chamber and the culture solution storage chamber.

The storage tank may have the plurality of cell culture units, and a gas flow path that allows the plurality of cell culture units to communicate with each other, and the gas flow path may be configured to circulate the culture solution between the plurality of cell culture units by simultaneously pressurizing insides of the plurality of cell culture units.

According to a second aspect of the present invention, a cell culture method is provided, including: preparing a cell culture apparatus that includes a storage tank having one or a plurality of cell culture units in which the cell culture unit includes a culture chamber having an inner surface-side space in which a culture solution is stored, a permeable membrane having a first surface to which cells are adherable and a second surface opposite to the first surface, the first surface facing the inner surface-side space, a culture solution storage chamber that stores the culture solution, and a culture solution introduction flow path that introduces the culture solution in the culture solution storage chamber to the inner surface-side space; and allowing the culture solution to permeate through the membrane from the inner surface-side space and flow into an outer surface-side space that the second surface of the membrane faces, in a state where the cells adhere to the first surface of the membrane facing the inner surface-side space.

The cells may include hepatocytes and vascular endothelial cells.

When the cells adhere to the membrane, a cell cluster including the hepatocytes and the vascular endothelial cells may be formed, and the cell cluster may be seeded on the membrane.

The culture chamber and the culture solution storage chamber may have vent holes through which gas is supplied to and discharged from the culture chamber and the culture solution storage chamber, and gas may be supplied to and discharged from the culture chamber and the culture solution storage chamber via the vent holes.

The storage tank may have the plurality of cell culture units, and a gas flow path that allows the plurality of cell culture units to communicate with each other, and the culture solution may be circulated between the plurality of cell culture units by simultaneously pressurizing insides of the plurality of cell culture units via the gas flow path.

Advantageous Effects of Invention

According to the above aspect of the present invention, a culture solution introduction flow path that introduces a culture solution of a culture solution storage chamber to an inner surface-side space of a culture chamber, and a culture solution discharge flow path that sends the culture solution of an outer surface-side space to the culture solution storage chamber are provided. Therefore, in a case where a step of increasing the pressure in the inner surface-side space and a step of decreasing the pressure in the inner surface-side space are repeated, cells can be cultured while changing the pressure applied to the cells in an environment where the culture solution is perfused. Therefore, for example, in culture of cells including hepatocytes and vascular endothelial cells, a luminal structure of vascular endothelial cells can be formed. Thus, in the cells, a three-dimensional tissue capable of reproducing physiological functions in vivo can be constructed, and the three-dimensional tissue capable of reproducing physiological functions in vivo can be maintained for a long time. Accordingly, it is possible to accurately evaluate a test sample such as a pharmaceutical drug candidate.

BEST MODE FOR CARRYING OUT THE INVENTION

First Embodiment

[Cell Culture Apparatus]

A cell culture apparatus according to a first embodiment of the present invention includes a storage tank having one or a plurality of cell culture units, in which the cell culture unit includes a culture chamber having an inner surface-side space in which a culture solution is stored, a permeable membrane having a first surface to which cells are adherable and a second surface opposite to the first surface, the first surface facing the inner surface-side space, a culture solution storage chamber that stores the culture solution, a culture solution introduction flow path that introduces the culture solution in the culture solution storage chamber to the inner surface-side space, and a culture solution discharge flow path that sends, to the culture solution storage chamber, the culture solution which permeates through the membrane from the inner surface-side space and flows into an outer surface-side space that the second surface of the membrane faces.

A cell culture apparatus 10 according to the first embodiment will be described with reference to the drawings.

Figure 1:
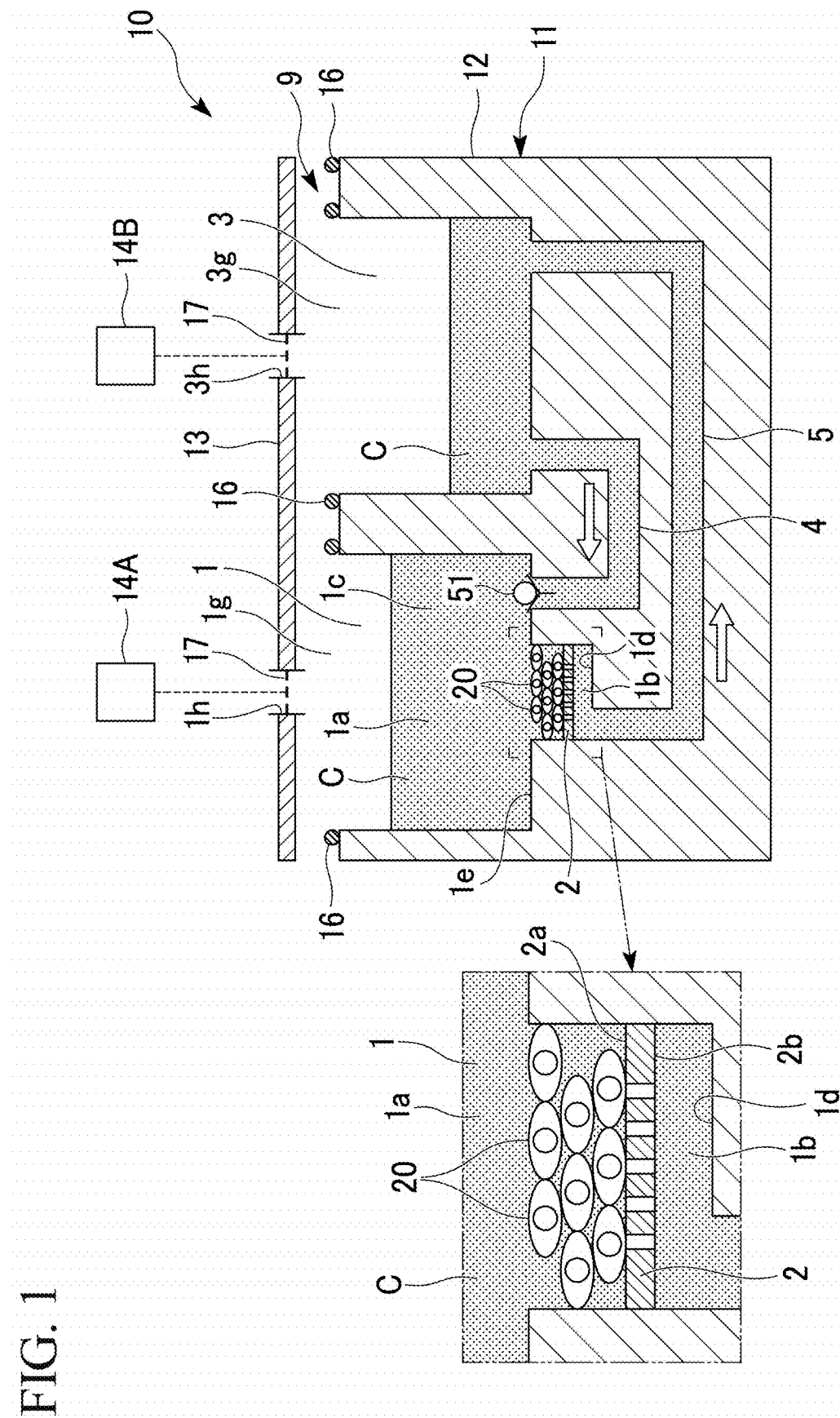
FIG. 1 is a schematic view schematically showing a cell culture apparatus according to a first embodiment.
Figure 2:
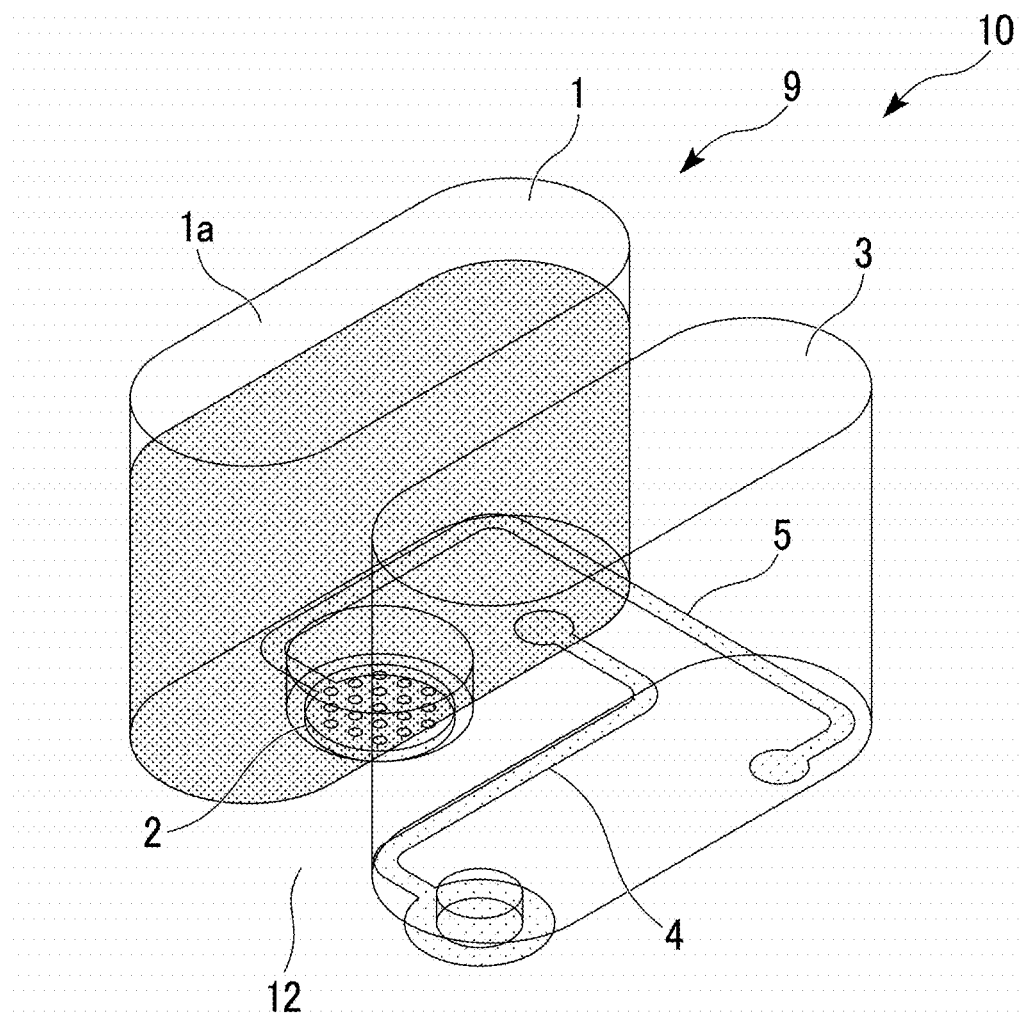
FIG. 2 is a perspective view schematically showing the cell culture apparatus of FIG. 1.

FIG. 1 is a schematic view schematically showing the cell culture apparatus 10. FIG. 2 is a perspective view schematically showing a part of the cell culture apparatus 10.

As shown in FIG. 1, the cell culture apparatus 10 includes a storage tank 11. The storage tank 11 includes a container-shaped tank main body 12 and a lid portion 13, and forms one cell culture unit 9.

As shown in FIGS. 1 and 2, the cell culture unit 9 includes a culture chamber 1, a membrane 2, a culture solution storage chamber 3, a culture solution introduction flow path 4, and a culture solution discharge flow path 5.

The culture chamber 1 and the culture solution storage chamber 3 are spaces secured by a cavity formed in the tank main body 12 of the storage tank 11, and can store a culture solution C (a liquid).

As shown in FIG. 1, the culture chamber 1 has a main chamber 1c and a cavity 1d formed on a bottom surface 1e of the main chamber 1c. An internal space of the main chamber 1c and an internal space of an upper part of the concavity 1d are an inner surface-side space 1a. A space which is an internal space of a lower part of the concavity 1d and is partitioned by the membrane 2 is an outer surface-side space 1b. The outer surface-side space 1b is located below the membrane 2. The culture chamber 1 can store the culture solution C.

In the culture chamber 1, the membrane 2 separates the inner surface-side space 1a and the outer surface-side space 1b. The membrane 2 is located at a position higher than that of a bottom surface of the concavity 1d. An inner surface 2a (one surface, a first surface) of the membrane 2 faces the inner surface-side space 1a, and an outer surface 2b (the other surface, a second surface) faces the outer surface-side space 1b.

The membrane 2 can allow a fluid to permeate therethrough due to a pressure difference between the inner surface-side space and the outer surface-side space. Cells 20 cannot permeate through the membrane 2.

The membrane 2 may be a porous membrane. An average pore diameter of the membrane 2 is, for example, 0.1 μm to 10 μm. A size of a pore of the membrane 2 is such a size that the liquid can pass but the cells 20 cannot pass (the membrane 2 has permeability for the liquid). A material of the membrane 2 is, for example, polycarbonate, polyester, a silicone resin, or the like.

It is preferable that the inner surface 2a of the membrane 2 be coated with a cell adhesive material. As the cell adhesive material, for example, a protein having cell adhesiveness can be used. As the cell adhesive material, gelatin, collagen, fibronectin, laminin, vitronectin, matrigel, polylysine, or the like can be used.

A thickness of the membrane 2 is preferably 0.1 to 100 μm.

One end (a first end) of the culture solution introduction flow path 4 is connected to a bottom portion of the culture solution storage chamber 3, and the other end (a second end) thereof is connected to a bottom portion of the main chamber 1c of the culture chamber 1. The culture solution storage chamber 3 and the inner surface-side space 1a communicate with each other through the culture solution introduction flow path 4. The culture solution introduction flow path 4 can introduce the culture solution C in the culture solution storage chamber 3 to the inner surface-side space 1a.

One end (a first end) of the culture solution discharge flow path 5 is connected to a bottom portion of the concavity 1d, and the other end (a second end) thereof is connected to a bottom portion of the culture solution storage chamber 3. The culture solution storage chamber 3 and the outer surface-side space 1b communicate with each other through the culture solution discharge flow path 5. The culture solution discharge flow path 5 can introduce the culture solution C in the outer surface-side space 1b to the culture solution storage chamber 3.

The lid portion 13 airtightly closes an opening of the tank main body 12 in an openable manner. Specifically, the lid portion 13 can airtightly close the upper openings of the culture chamber 1 and the culture solution storage chamber 3.

The lid portion 13 has vent holes 1h and 3h at positions corresponding to the culture chamber 1 and the culture solution storage chamber 3. It is possible to supply gas (for example, air) to the culture chamber 1 and the culture solution storage chamber 3, and discharge gas (for example, air) from the culture chamber 1 and the culture solution storage chamber 3 through the vent holes 1h and 3h, respectively. An air filter 17 is preferably provided in each of the vent holes 1h and 3h. The air filter 17 can prevent foreign matter from entering the culture chamber 1 and the culture solution storage chamber 3.

Gas (for example, air) can be supplied to the main chamber 1c of the culture chamber 1 through the vent hole 1h using a first pressure-adjusting unit 14A, which is a pressurizing pump such as a compressor. Gas (for example, air) can be supplied to the culture solution storage chamber 3 through the vent hole 3h using a second pressure-adjusting unit 14B, which is a pressurizing pump such as a compressor.

In the cell culture apparatus 10 of FIG. 1, the pressure-adjusting units 14A and 14B supply gas, whereby the pressure in the culture chamber 1 (specifically, the inner surface-side space 1a) and the culture solution storage chamber 3 can be adjusted, but a structure for adjusting the pressure of the culture chamber 1 (the inner surface-side space 1a) and the culture solution storage chamber 3 is not limited to the pressure-adjusting units 14A and 14B. For example, a structure in which a culture solution is supplied to the culture chamber 1 and the culture solution storage chamber 3 by the head pressure to increase the pressure in the culture chamber 1 (the inner surface-side space 1a) and the culture solution storage chamber 3 may be adopted.

In the culture chamber 1, a check valve 51 is provided at the other end (the second end) of the culture solution introduction flow path 4. The check valve 51 allows a flow of the culture solution C (a flow in a forward direction) from the culture solution introduction flow path 4 toward the inner surface-side space 1a, and prevents a flow in a reverse direction thereof (a flow of the culture solution C from the inner surface-side space 1a toward the culture solution introduction flow path 4).

As the check valve 51, for example, a check valve having a structure that includes a valve seat having a valve hole and a valve body can be exemplified. In the check valve having this structure, when the liquid flows in the forward direction, the valve body is separated from the valve seat to open the valve hole. Thus, the liquid flows in the forward direction through the valve hole. When the liquid flows in the reverse direction, the valve body abuts on the valve seat and the valve hole is closed. Thus, the flow of the liquid in that direction (the flow of the liquid in the reverse direction) is prevented.

The check valve 51 is an example of a backflow prevention mechanism that regulates a flow of a culture solution. The check valve 51 can prevent a flow in a direction reverse to a direction of a circulation flow of the culture solution C (a flow returning back to the culture solution storage chamber 3 via the inner surface-side space 1a, the membrane 2, and the outer surface-side space 1b from the culture solution storage chamber 3).

[Cell Culture Method]

Next, an example of a method for culturing cells using the cell culture apparatus 10 will be described.

According to the present embodiment, a cell culture method is provided, including: preparing a cell culture apparatus that includes a storage tank having one or a plurality of cell culture units in which the cell culture unit includes a culture chamber having an inner surface-side space in which a culture solution is stored, a permeable membrane having a first surface to which cells are adherable and a second surface opposite to the first surface, the first surface facing the inner surface-side space, a culture solution storage chamber that stores the culture solution, and a culture solution introduction flow path that introduces the culture solution in the culture solution storage chamber to the inner surface-side space; and allowing the culture solution to permeate through the membrane from the inner surface-side space and flow into an outer surface-side space that the second surface of the membrane faces, in a state where the cells adhere to the first surface of the membrane facing the inner surface-side space.

The cells 20 are seeded on the inner surface 2a of the membrane 2 and are made to adhere thereto, and the culture solution C is introduced into the culture chamber 1 and the culture solution storage chamber 3. Examples of the cells 20 include hepatocytes. The cells 20 preferably include hepatocytes and vascular endothelial cells, for example. The cells 20 preferably form a plurality of layers on the inner surface 2a of the membrane 2. The cells 20 constituting the plurality of layers have a three-dimensional structure.

In adhesion of the cells 20 to the membrane 2, it is preferable to coat an inner surface-side (the inner surface 2a) of the membrane 2 with the cell adhesive material in advance. In addition, in a case of introducing the cells 20 into the membrane 2, for example, a method of introducing a suspension of hepatocytes and vascular endothelial cells into the inner surface-side (the inner surface 2a) of the membrane 2 is possible. A method of forming a cell cluster (spheroid or liver bud) including hepatocytes and vascular endothelial cells and seeding the cell cluster on the membrane 2 is also possible.

(1) Step 1

The lid portion 13 is closed so as to be pressed against a packing 16, and upper openings 1g and 3g of the culture chamber 1 and the culture solution storage chamber 3 are airtightly closed.

Gas (for example, air) is supplied to the culture chamber 1 through the vent hole 1h to pressurize the culture chamber 1 (specifically, the inner surface-side space 1a). In this case, the culture solution storage chamber 3 is preferably open to the atmosphere through the vent hole 3h.

Due to the pressure in the inner surface-side space 1a being higher than the pressure in the outer surface-side space 1b, part of the culture solution C in the inner surface-side space 1a permeates through the membrane 2 and moves to the outer surface-side space 1b. Thereby, a flow of the culture solution C that is sent from the inner surface-side space 1a of the culture chamber 1 to the culture solution storage chamber 3 through the culture solution discharge flow path 5, via the membrane 2 and the outer surface-side space 1b is generated. At this time, the cells 20 do not permeate through the membrane 2.

Since the culture chamber 1 has the check valve 51, the culture solution C in the inner surface-side space 1a does not flow into the culture solution introduction flow path 4.

(2) Step 2

Gas (for example, air) is supplied to the culture solution storage chamber 3 through the vent hole 3h to pressurize the culture solution storage chamber 3. In this case, the culture chamber 1 is preferably open to the atmosphere through the vent hole 1h.

Due to the pressure in the culture solution storage chamber 3 being higher than the pressure in the inner surface-side space 1a, part of the culture solution C in the culture solution storage chamber 3 is introduced into the inner surface-side space 1a of the culture chamber 1 through the culture solution introduction flow path 4.

Since the cells 20 are adhered to the membrane 2, the fluid resistance thereof is generally larger than the fluid resistance of the culture solution introduction flow path 4. Therefore, the culture solution C in the culture solution storage chamber 3 is mainly introduced into the inner surface-side space 1a of the culture chamber 1 through the culture solution introduction flow path 4, and the amount of flow through the culture solution discharge flow path 5 is small. In particular, in a case where the cells 20 have the three-dimensional structure having the plurality of layers, the fluid resistance is increased by the membrane 2 to which the cells 20 having the three-dimensional structure are adhered. Thus, the culture solution C in the culture solution storage chamber 3 hardly flows into the culture solution discharge flow path 5.

By repeating Step 1 and Step 2, a flow (circulation flow) of the culture solution C that permeates through the membrane 2 from the inner surface-side space 1a of the culture chamber 1 is sent to the culture solution storage chamber 3 via the outer surface-side space 1b and returns back to the inner surface-side space 1a of the culture chamber 1 can be generated. By allowing the culture solution C to flow in a permeation direction of the membrane 2, a sufficient amount of the culture solution C can be supplied to the entirety of the cells 20 having the three-dimensional structure in a thickness direction.

Specifically, for example, the cell culture method according to the present embodiment can be applied to the following tests.

By adding a substance as a test sample into a system (for example, the inner surface-side space 1a of the culture chamber 1), the influence of the substance as the test sample on the cells 20 can be evaluated. Examples of the substance as the test sample include a pharmaceutical candidate substance and chemical substances used in other chemical products (food additives, cosmetic raw materials, paints, agricultural chemicals, and the like).

The cell culture apparatus 10 includes the culture solution introduction flow path 4 that introduces the culture solution C in the culture solution storage chamber 3 into the inner surface-side space 1a, and the culture solution discharge flow path 5 that sends the culture solution C in the outer surface-side space 1b to the culture solution storage chamber 3. Therefore, in a case where Step 1 of increasing the pressure in the inner surface-side space 1a and Step 2 of decreasing the pressure in the inner surface-side space 1a are repeated, the cells 20 can be cultured while changing the pressure applied to the cells 20 in an environment where the culture solution C is perfused. Therefore, for example, in culture of the cells 20 including hepatocytes and vascular endothelial cells, a luminal structure of vascular endothelial cells can be formed. Thus, in the cells 20, a three-dimensional tissue capable of reproducing physiological functions in vivo can be constructed, and the three-dimensional tissue capable of reproducing physiological functions in vivo can be maintained for a long time. Accordingly, it is possible to accurately evaluate a test sample such as a pharmaceutical candidate substance.

In the cell culture apparatus 10, since circulating use of the culture solution C is possible, the test sample can be continuously exposed to the cells 20, and the amount of the culture solution C used can be reduced. In addition, since the lid portion 13 is configured to be openable and closable, aseptic operation is also facilitated.

Since the cell culture apparatus 10 has a simple structure such as a flow path, the apparatus structure can be simplified to reduce the size of the apparatus, and operation such as setting of the apparatus can be facilitated.

First Modification Example of First Embodiment

Figure 3:
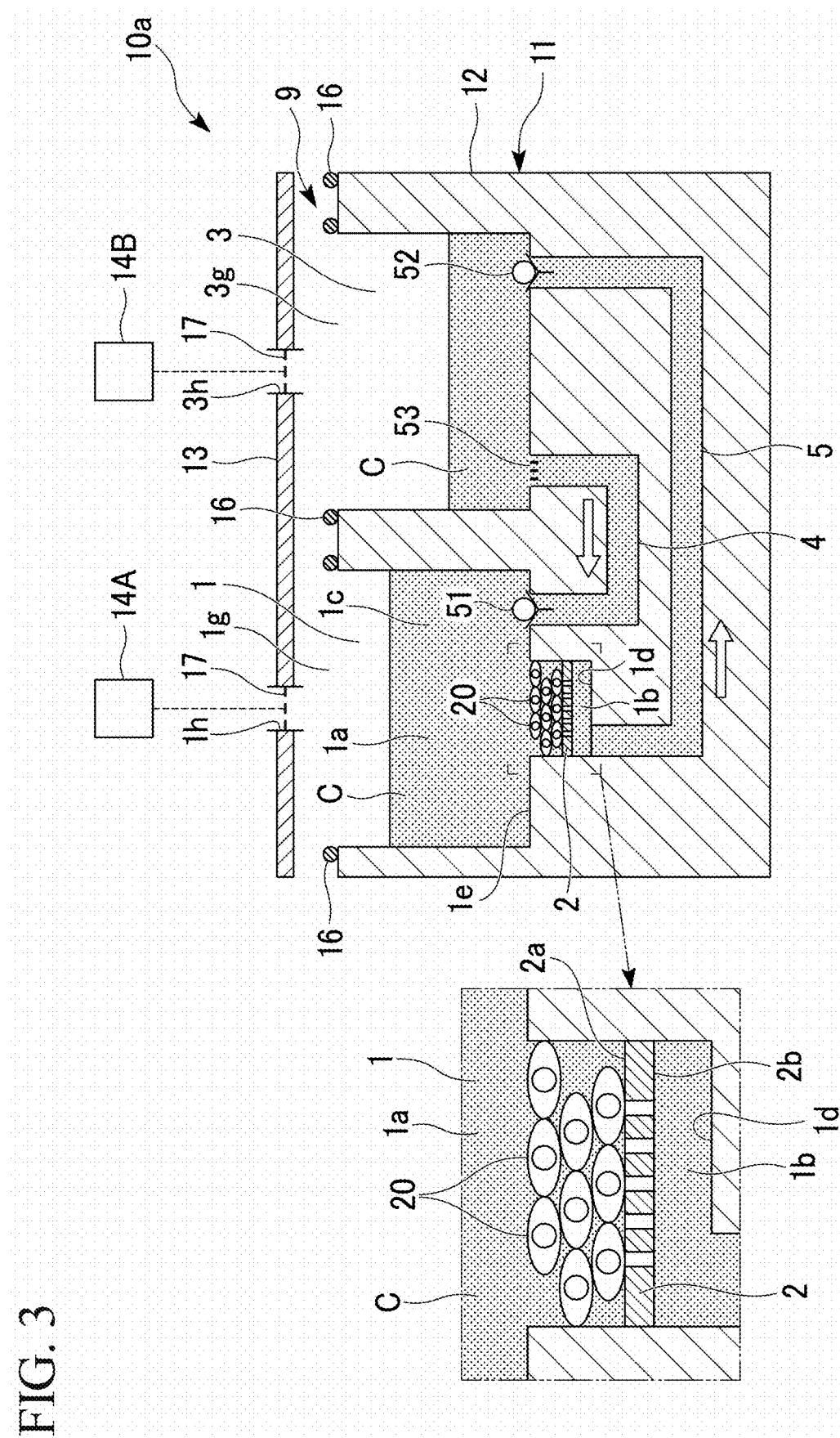
FIG. 3 is a schematic view showing a first modification example of the cell culture apparatus of FIG. 1.

A first modification example of the cell culture apparatus 10 according to the first embodiment will be described with reference to FIG. 3. FIG. 3 is a schematic view showing a cell culture apparatus 10a as a modification example of the cell culture apparatus 10. The same components as those already described are denoted by the same reference numerals and description thereof will be omitted.

As shown in FIG. 3, in the culture solution storage chamber 3, a check valve 52 is provided at the other end (the second end) of the culture solution discharge flow path 5. The check valve 52 allows a flow of the culture solution C from the culture solution discharge flow path 5 toward the culture solution storage chamber 3, and prevents a flow in a reverse direction thereof (a flow from the culture solution storage chamber 3 to the culture solution discharge flow path 5). Since the check valve 52 is provided in the culture solution storage chamber 3, in Step 2, the culture solution C in the culture solution storage chamber 3 does not flow into the culture solution discharge flow path 5.

A Laplace valve 53 is provided at one end (the first end) of the culture solution introduction flow path 4. The Laplace valve 53 allows a flow of the culture solution C from the culture solution storage chamber 3 to the culture solution introduction flow path 4 and prevents an inflow of gas (for example, air).

The Laplace valve 53 can prevent the flow in the direction reverse to the direction of the circulation flow of the culture solution C (the flow returning back to the culture solution storage chamber 3 via the inner surface-side space 1a, the membrane 2, and the outer surface-side space 1b from the culture solution storage chamber 3).

Figure 8:
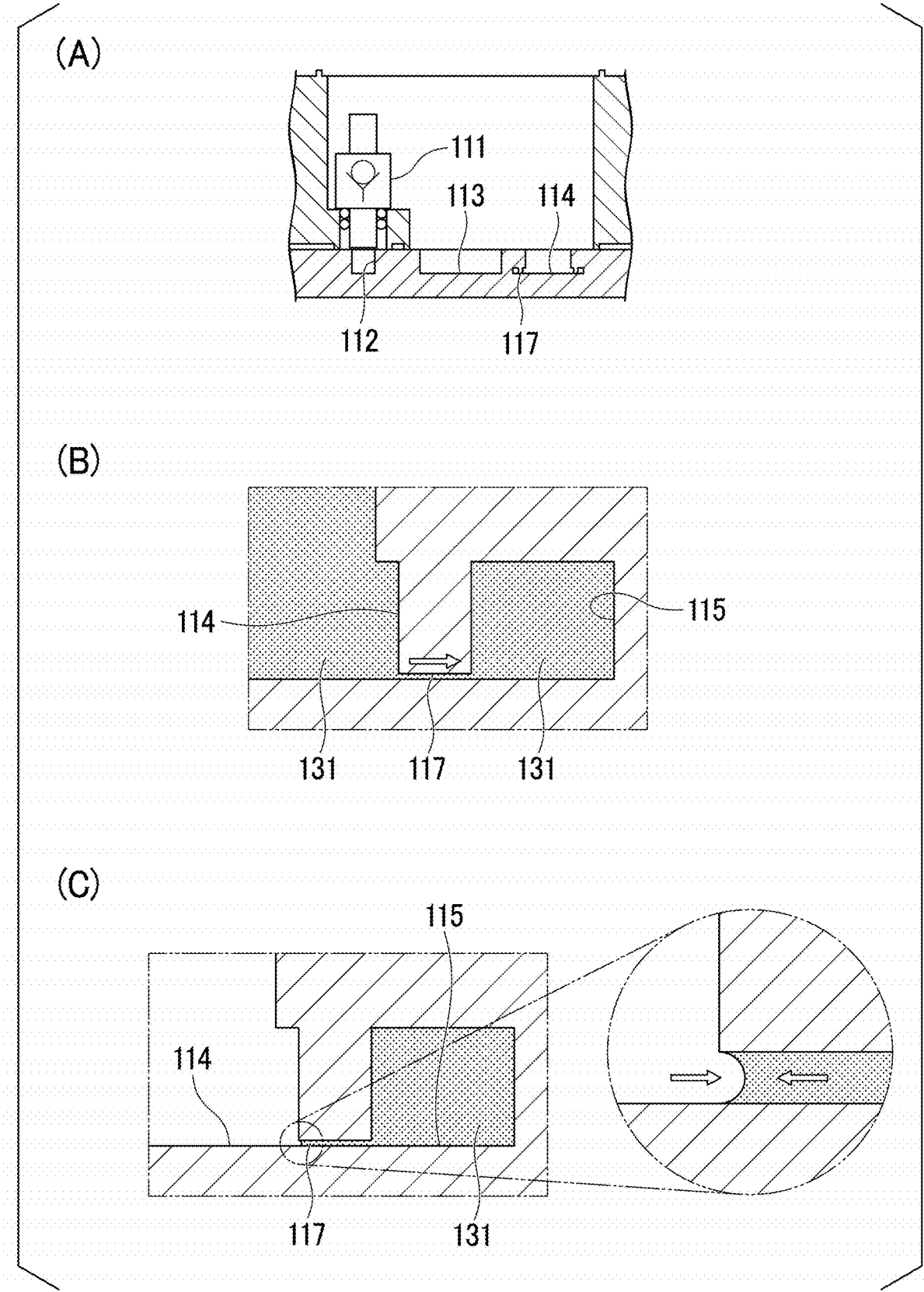
FIG. 8 is an explanatory view of a Laplace valve, (A) is a partially enlarged view of a liquid storage chamber provided with the Laplace valve, (B) is a typical view of a case where a medium flows into a connecting flow path from a downstream port via the Laplace valve, and (C) is a typical view of a case where the Laplace valve functions when air flows into the downstream port.

The structure and function of the Laplace valve 53 will be described with reference to FIGS. 8(A) to 8(C). FIG. 8(A) shows a partially enlarged view of a liquid storage chamber provided with a Laplace valve 117. FIG. 8(B) shows a typical view of a case where a medium 131 flows from a downstream port 114 into a connecting flow path 115 via the Laplace valve 117. FIG. 8(C) shows a typical view of a case where the Laplace valve 117 functions when air flows into the downstream port 114. As shown in FIG. 8(C), a pressure difference due to interfacial tension, that is, a Laplace pressure is generated between the medium 131 and air in the micro-flow path. In a case where the surface of the flow path is wet with a liquid medium, air cannot flow into the micro-flow path filled with a liquid under a condition of an air pressure lower than the Laplace pressure. Under such a condition, the micro-flow path can be treated as a passive air inflow prevention mechanism.

The design of the Laplace valve will be described below.

A pressure (Laplace pressure, critical pressure) ($\Delta P_{Lap}$) at which air flows into the Laplace valve can be calculated by an interfacial tension ($\gamma$), and a width ($w_L$) and a depth ($h_L$) of the micro-flow path constituting the Laplace valve using the following Equation (1).

[Expression 1]

$$\Delta P_{Lap} = 2\gamma(1/w_L + 1/h_L) \qquad (1)$$

It is considered that a practical pressure range for driving the cell culture apparatus is determined by a pressure range adjustable with a commercially available pressure controller and a pressure resistance of cells.

Assuming that the pressure resistance of cells is about an upper limit (30 kPa=225 mmHg) of blood pressure in the living body, a practical pressure range for driving the cell culture apparatus according to the present embodiment is about 1 kPa to 30 kPa. In a case where the interfacial tension of a culture solution is about 60 mN/m and a section of the micro-flow path constituting the Laplace valve is square, that is, in a case where $w_L = h_L$, a dimension (length) of the micro-flow path into which air flows at 30 kPa is estimated as about $w_L = h_L = 8$ µm and a dimension (length) of the micro-flow path into which air flows at 1 kPa is estimated as about $w_L = h_L = 240$ µm, using Equation (1).

By setting the dimensions of the micro-flow path constituting the Laplace valve to be smaller than the above-described dimensions ($w_L = h_L = 8$ µm at 30 kPa and $w_L = h_L = 240$ µm at 1 kPa), it is possible to prevent air from flowing into the Laplace valve when the apparatus is operated at a predetermined pressure.

That is, when the micro-flow path constituting the Laplace valve is formed so that the Laplace pressure $\Delta P_{Lap}$ which is a critical pressure for the Laplace valve to function is larger than the pressure range used in the cell culture apparatus according to the present embodiment, it is possible to prevent air from flowing into the Laplace valve.

Even in a case where a ratio of $w_L$ to $h_L$ is not 1:1, it is possible to similarly design the dimension of the flow path based on Equation (1).

The Laplace valve 53 is an example of the backflow prevention mechanism that regulates the flow of the culture solution.

Second Modification Example of First Embodiment

Figure 4:
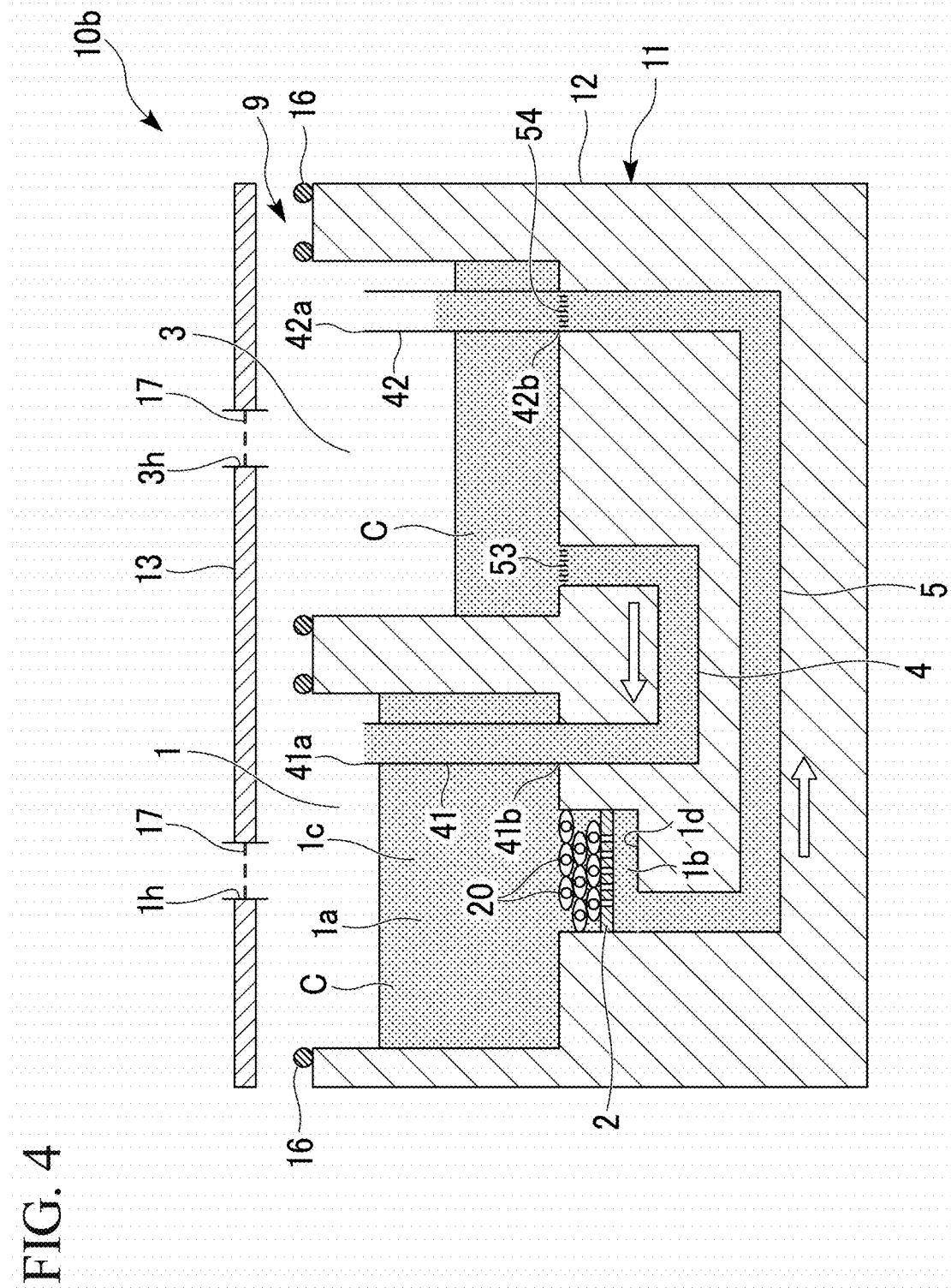
FIG. 4 is a schematic view showing a second modification example of the cell culture apparatus of FIG. 1.
Figure 5:
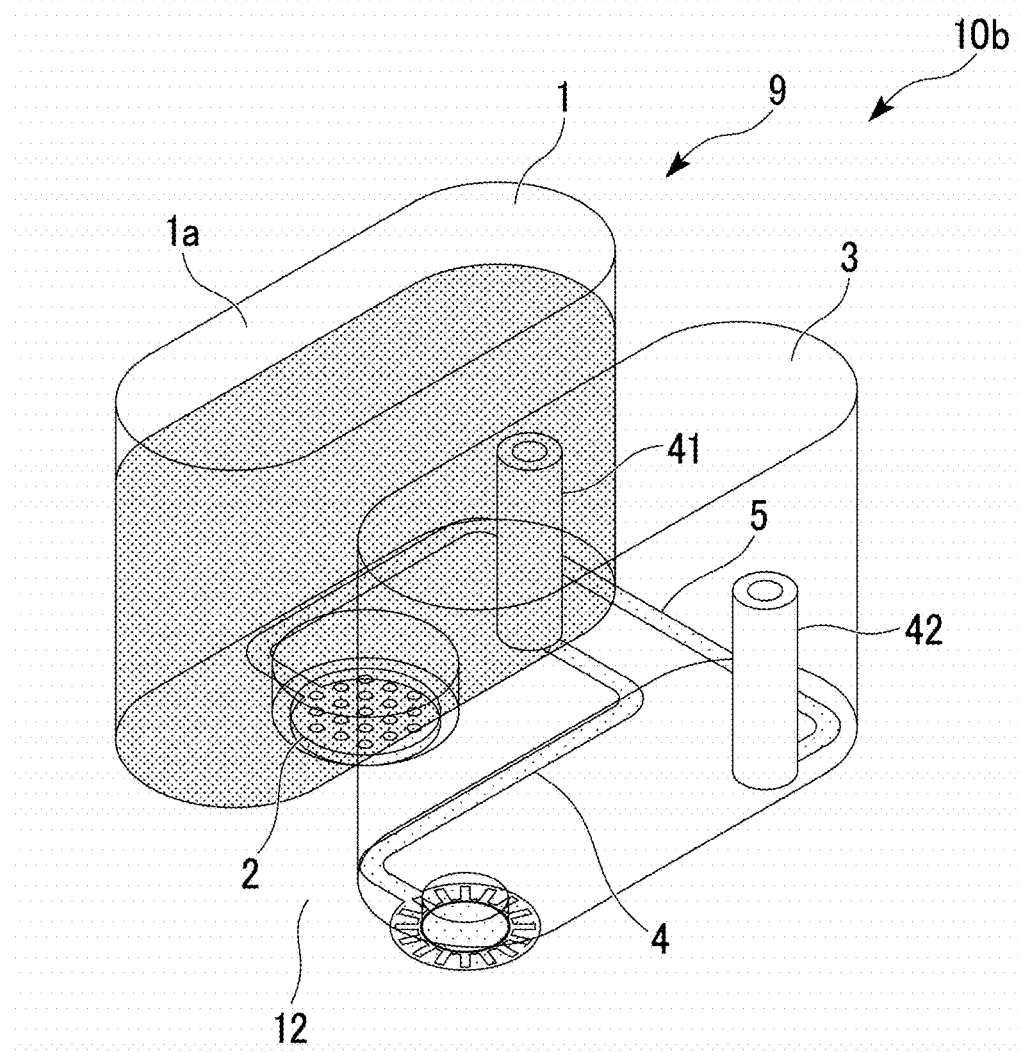
FIG. 5 is a perspective view schematically showing the cell culture apparatus of FIG. 4.

A second modification example of the cell culture apparatus 10 according to the first embodiment will be described with reference to FIG. 4 and FIG. 5. FIG. 4 is a schematic view showing a cell culture apparatus 10b as a modification example of the cell culture apparatus 10. FIG. 5 is a perspective view schematically showing the cell culture apparatus 10b. The same components as those already described are denoted by the same reference numerals and description thereof will be omitted. In FIG. 4, the first pressure-adjusting unit 14A and the second pressure-adjusting unit 14B (see FIG. 1) are omitted.

As shown in FIG. 4 and FIG. 5, in the main chamber 1c of the culture chamber 1, an extension pipeline (extension cylinder) 41 that is connected to the other end (the second end) of the culture solution introduction flow path 4 and extends upward is provided. An upper end opening 41a of the extension pipeline 41 is located at a position higher than that of a base end 41b of the extension pipeline 41.

In the culture solution storage chamber 3, an extension pipeline 42 that is connected to the other end (the second end) of the culture solution discharge flow path 5 and extends upward is provided. An upper end opening 42a of the extension cylinder 42 is located at a position higher than that of a base end 42b of the extension cylinder 42.

A Laplace valve 54 is provided at the other end (the second end) of the culture solution discharge flow path 5. The Laplace valve 54 allows a flow of the culture solution C from the culture solution discharge flow path 5 to the culture solution storage chamber 3 and prevents an inflow of gas (for example, air).

In Step 1, the culture solution C in the extension pipeline 41 and the culture solution introduction flow path 4 can flow into the culture solution storage chamber 3 as the pressure in the culture chamber 1 (specifically, the inner surface-side space 1a) increases, but at the time when the culture solution C in the extension pipeline 41 and the culture solution introduction flow path 4 runs out, the Laplace valve 53 stops the flow of the culture solution C into the culture solution storage chamber 3 via the culture solution introduction flow path 4. On the other hand, the flow of the culture solution C from the culture chamber 1 toward the culture solution storage chamber 3 via the membrane 2 and the culture solution discharge flow path 5 is allowed.

The culture solution C flows into the culture solution storage chamber 3 from the upper end opening 42a of the extension pipeline 42. Therefore, a circulation flow of the culture solution C (a flow returning back to the inner surface-side space 1a of the culture chamber 1 via the membrane 2, the outer surface-side space 1b, the culture solution discharge flow path 5, and the culture solution storage chamber 3 from the inner surface-side space 1a of the culture chamber 1) is allowed, and a flow in a reverse direction is regulated.

In Step 2, the culture solution C in the extension cylinder 42 can flow into the culture solution discharge flow path 5 as the pressure in the culture solution storage chamber 3 increases, but at the time when the culture solution C in the extension cylinder 42 runs out, the Laplace valve 54 stops the flow of the culture solution C into the culture solution discharge flow path 5. On the other hand, the flow of the culture solution C from the culture solution storage chamber 3 toward the culture chamber 1 via the culture solution introduction flow path 4 is allowed. The culture solution C flows into the main chamber 1c of the culture chamber 1 from the upper end opening 41a of the extension pipeline 41. Therefore, the circulation flow of the culture solution C is allowed, and the flow in the reverse direction is regulated.

Similarly to the first embodiment, the cell culture apparatus 10b can culture the cells 20 while changing the pressure applied to the cells 20 in an environment where the culture solution C is perfused. Therefore, for example, in culture of the cells 20 including hepatocytes and vascular endothelial cells, a luminal structure of vascular endothelial cells can be formed. Thus, in the cells 20, a three-dimensional tissue capable of reproducing physiological functions in vivo can be constructed, and the three-dimensional tissue capable of reproducing physiological functions in vivo can be maintained for a long time. Accordingly, it is possible to accurately evaluate a test sample such as a pharmaceutical candidate substance.

Second Embodiment

[Cell Culture Apparatus]

Figure 6:
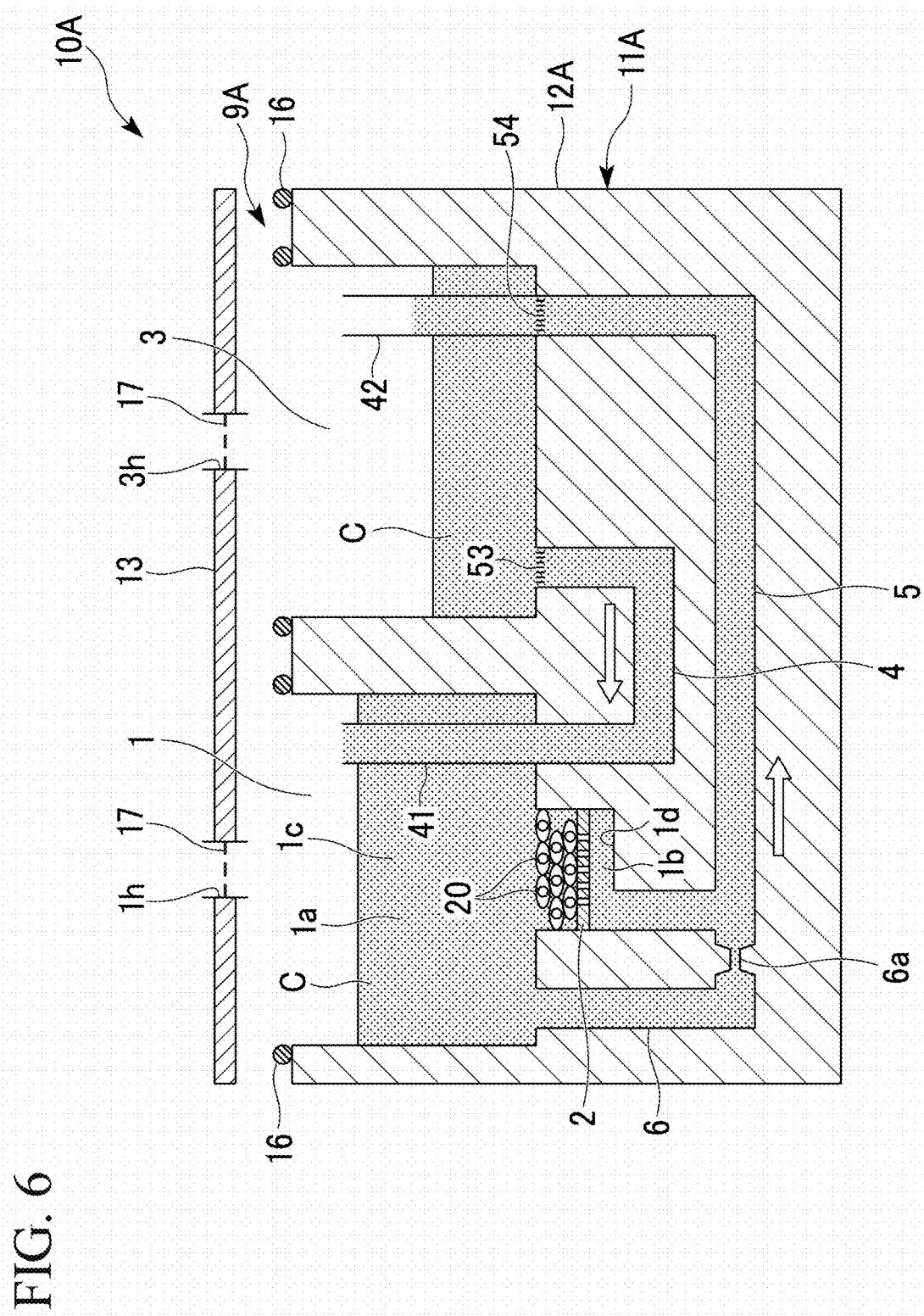
FIG. 6 is a schematic view schematically showing a cell culture apparatus according to a second embodiment.

A cell culture apparatus 10A according to a second embodiment will be described with reference to FIG. 6. FIG. 6 is a schematic view schematically showing the cell culture apparatus 10A. The same components as those already described are denoted by the same reference numerals and description thereof will be omitted.

As shown in FIG. 6, the cell culture apparatus 10A includes a storage tank 11A. The storage tank 11A includes a tank main body 12A and the lid portion 13, and forms a cell culture unit 9A.

The cell culture unit 9A includes the culture chamber 1, the membrane 2, the culture solution storage chamber 3, the culture solution introduction flow path 4, the culture solution discharge flow path 5, and a bypass flow path (a bypass path) 6. The cell culture unit 9A is different from the cell culture unit 9 (see FIG. 1) of the cell culture apparatus 10 according to the first embodiment in having the bypass flow path 6.

One end (a first end) of the bypass flow path 6 is connected to a bottom portion of the main chamber 1c of the culture chamber 1, and the other end (a second end) thereof is connected to the culture solution discharge flow path 5. The bypass flow path 6 can introduce the culture solution C in the inner surface-side space 1a into the culture solution discharge flow path 5 without passing through the membrane 2. Thereby, even in a case where it is difficult to circulate a liquid via the cells 20 of the three-dimensional tissue formed on the inner surface-side of the membrane 2, it is possible to circulate the culture solution in the cell culture apparatus 10A.

The bypass flow path 6 may have a resistance flow path part 6a of which a flow path sectional area (an area of a section orthogonal to a flow direction of the culture solution C) is smaller than the other part in the bypass flow path 6 (for example, the flow path sectional area is 1/10 or less of that of the other part).

The flow path sectional area of the resistance flow path part 6a may be, for example, 1/10 or less of the other part. In a case where the sectional area of the resistance flow path part 6a is 1/10 of the sectional area of the other part, a flow path resistance becomes 100 times that of the other part. A flow rate of a liquid can be adjusted by the resistance flow path part 6a.

The resistance flow path part 6a will be described.

A flow rate (Q) and a pressure loss (ΔP) of a liquid flowing through the micro-flow path having a rectangular section have the following relationship (see F. M. White, Viscous Fluid Flow, McGraw-Hill Companies, Inc, Boston, 2006).

[Expression 2]

$$\Delta P = R \times Q \quad (2)$$

[Expression 3]

$$R = \frac{12\mu l}{wh^3}\left\{1 - \frac{h}{w}\left[\frac{192}{\pi^5}\sum_{i=1,3,5}^{\infty}\frac{1}{i^5}\tanh\left(\frac{i\pi w}{2h}\right)\right]\right\}^{-1} \quad (3)$$

In Equations (2) and (3), ΔP represents a pressure difference between an inlet and an outlet of the micro-flow path, R represents a flow path resistance, μ represents a viscosity of a fluid, l represents a length of the micro-flow path, w represents a width of the micro-flow path, and h represents a depth of the micro-flow path. Equations (2) and (3) are established with a condition of w>h.

For example, in the culture solution discharge flow path 5 to which the resistance flow path part 6a is connected, a case where the length of the resistance flow path part is equal to a length of a part other than the resistance flow path part is considered. In a case where the sectional area of a resistance flow path is 1/10 of the sectional area of the other part, the width w and the depth h become 1/10^{0.5}, and the flow path resistance R of the resistance flow path of Equation (3) becomes 100 times the flow path resistance R of the part other than the resistance flow path. According to Equation (2), regarding the pressure loss, the pressure loss in the resistance flow path becomes 100 times the pressure loss of the part other than the resistance flow path.

In a case where a resistance flow path part having a flow path sectional area of 1/10 or less is formed in a part of the flow path, there is an advantage in that the design of a flow path network becomes easy by designing the flow path in consideration of only the pressure loss in the resistance flow path.

[Cell Culture Method]

Next, an example of a method for culturing cells using the cell culture apparatus 10A will be described.

(1) Step 1

Gas (for example, air) is supplied to the culture chamber 1 through the vent hole 1h to pressurize the culture chamber 1 (specifically, the inner surface-side space 1a). At this time, the culture solution storage chamber 3 is preferably open to the atmosphere through the vent hole 3h.

Due to the pressure in the inner surface-side space 1a being higher than the pressure in the outer surface-side space 1b, part of the culture solution C in the inner surface-side space 1a permeates through the membrane 2 and moves to the outer surface-side space 1b. By doing this, a flow of the culture solution C that is sent from the inner surface-side space 1a of the culture chamber 1 to the culture solution storage chamber 3 through the culture solution discharge flow path 5, via the membrane 2 and the outer surface-side space 1b is generated. In this case, the cells 20 do not permeate through the membrane 2.

In a case where a flow-through resistance of the cells 20 of the three-dimensional tissue formed on the membrane 2 or the inner surface-side of the membrane 2 is large, a flow rate of the culture solution C flowing from the inner surface-side space 1a to the outer surface-side space 1b through the membrane 2 becomes lower. However, since part of the culture solution C in the inner surface-side space 1a flows to the culture solution discharge flow path 5 through the bypass flow path 6, decrease in a circulation flow rate of the culture solution C can be prevented.

(2) Step 2

Gas (for example, air) is supplied to the culture solution storage chamber 3 through the vent hole 3h to pressurize the culture solution storage chamber 3. At this time, the culture chamber 1 is preferably open to the atmosphere through the vent hole 1h.

Due to the pressure in the culture solution storage chamber 3 being higher than the pressure in the inner surface-side space 1a, part of the culture solution C in the culture solution storage chamber 3 is introduced into the inner surface-side space 1a of the culture chamber 1 through the culture solution introduction flow path 4.

By repeating Step 1 and Step 2, a flow (circulation flow) of the culture solution C that permeates through the membrane 2 from the inner surface-side space 1a of the culture chamber 1 is sent to the culture solution storage chamber 3 via the outer surface-side space 1b and returns back to the inner surface-side space 1a of the culture chamber 1 can be generated. By allowing the culture solution C to flow in a permeation direction of the membrane 2, a sufficient amount of the culture solution C can be supplied to the entirety of the cells 20 having the three-dimensional structure in a thickness direction.

Similarly to the first embodiment, the cell culture apparatus 10A can culture the cells 20 while changing the pressure applied to the cells 20 in an environment where the culture solution C is perfused. Therefore, for example, in culture of the cells 20 including hepatocytes and vascular endothelial cells, a luminal structure of vascular endothelial cells can be formed. Thus, in the cells 20, a three-dimensional tissue capable of reproducing physiological functions in vivo can be constructed, and the three-dimensional tissue capable of reproducing physiological functions in vivo can be maintained for a long time. Accordingly, it is possible to accurately evaluate a test sample such as a pharmaceutical candidate substance.

Since the cell culture apparatus 10A can prevent a decrease in the circulation flow rate of the culture solution C even in a case where a permeation resistance of the membrane 2 is large, an environment in which the culture solution C is perfused in the culture chamber 1 can be maintained. Therefore, transport of substance in the cells 20 and the membrane 2 can be improved. Thus, in the cells 20, the above-described three-dimensional tissue can be maintained for a long time while maintaining physiological functions.

Third Embodiment

Figure 7:
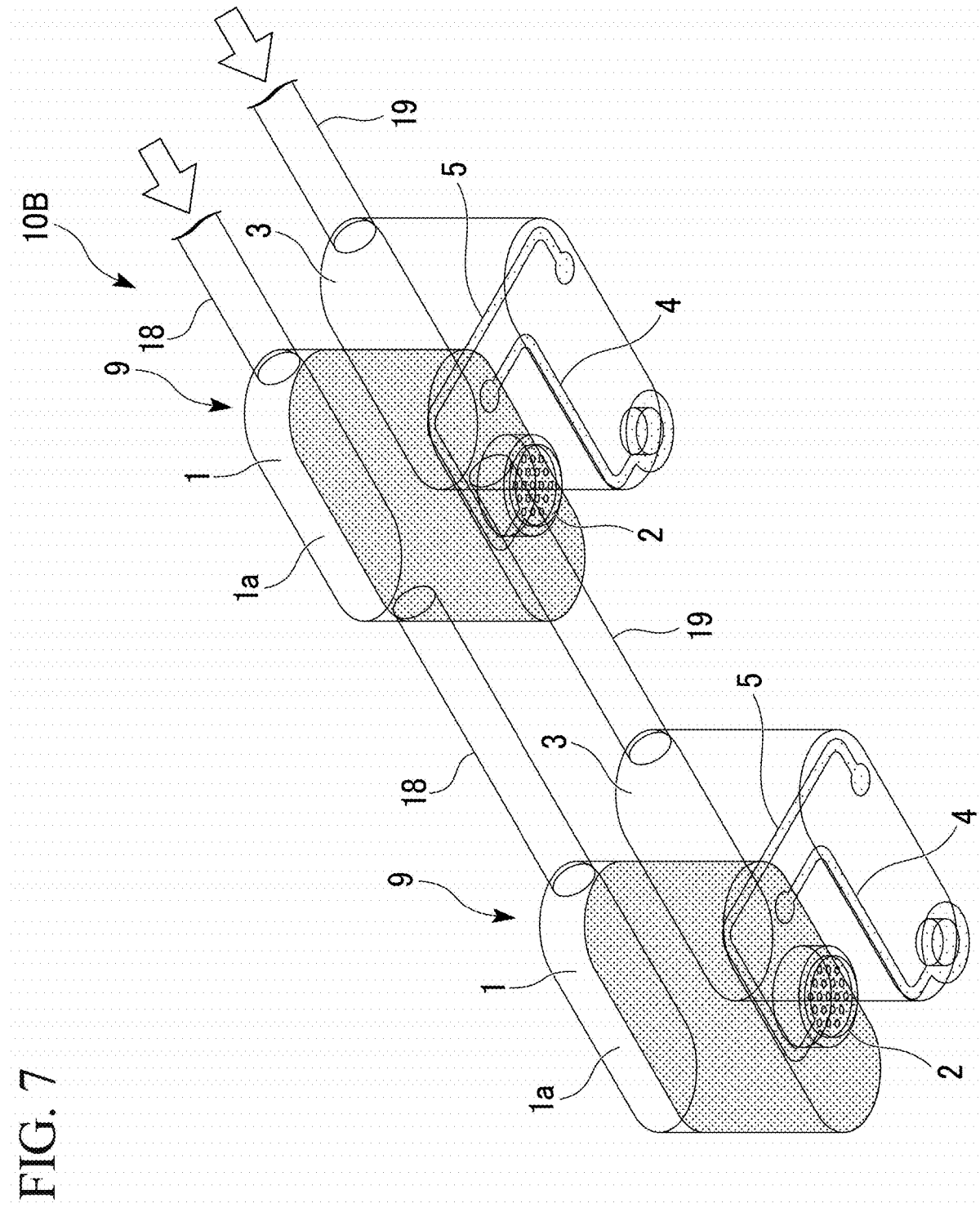
FIG. 7 is a schematic view schematically showing a cell culture apparatus according to a third embodiment.

A cell culture apparatus 10B according to a third embodiment will be described with reference to FIG. 7. FIG. 7 is a schematic view schematically showing the cell culture apparatus 10B. The same components as those already described are denoted by the same reference numerals and description thereof will be omitted.

The cell culture apparatus 10B has a plurality of the cell culture units 9 (see FIGS. 1 and 2).

At least two of the culture chambers 1 of the plurality of cell culture units 9 communicate with each other through, for example, a gas flow path (a first gas flow path) 18 formed in the lid portion 13 (see FIG. 1).

It is preferable that at least two of the culture solution storage chambers 3 of the plurality of cell culture units 9 communicate with each other through, for example, a gas flow path (a second gas flow path) 19 formed in the lid portion 13 (see FIG. 1).

In the cell culture apparatus 10B, since the plurality of cell culture units 9 communicate with each other through the gas flow path 18, the culture chambers 1 of the plurality of cell culture units 9 can be simultaneously pressurized. In a case where a plurality of the culture solution storage chambers 3 communicate with each other through a gas flow path (not shown), the culture solution storage chambers 3 of the plurality of cell culture units 9 can be simultaneously pressurized. Therefore, in the cell culture apparatus 10B, tests on the plurality of cell culture units 9 can be performed in parallel with ease. Accordingly, it is possible to perform a highly efficient test in drug discovery screening and the like.

For example, NPL 8 discloses a method of performing perfusion culture of a three-dimensional tissue by using a visceral peristaltic pump for liquid feeding.

In general, in a case of using a visceral peristaltic pump for liquid feeding, cell tissue culture is performed under a flow condition of a constant flow rate regardless of a structure in the three-dimensional tissue. In this case, for example, when vascular tissue is not developed in the three-dimensional tissue, an excessive liquid-feeding load is applied to the cell tissue.

On the other hand, according to the cell culture apparatus and the cell culture method according to the above-described embodiment, a configuration is provided in which a culture solution is circulated by repeating pressurization and release of atmospheric pressure via vent holes installed in a culture chamber and a culture solution storage chamber.

That is, in a liquid-feeding method by pressure drive in the above-described embodiment, since the culture solution is fed while being pressurized at a constant pressure, a flow rate of the culture solution is adjusted according to development of the vascular tissue in the three-dimensional tissue.

In the cell culture apparatus and the cell culture method according to the above-described embodiment, hepatocytes and vascular endothelial cells can be co-cultured under perfusion conditions, and a three-dimensional tissue of hepatocytes having a blood vessel-like structure can be constructed and cultured. Accordingly, it can be expected that a large amount of cells can be cultured even in a small culture area while maintaining expression of metabolic enzymes and the like.

Further, according to the cell culture apparatus and the cell culture method according to the above-described embodiment, a larger number of cells can be introduced into a culture container and cultured as compared with a culture method in the related art, for example, the cells of about 80 times per area can be introduced into the culture container and cultured.

In general, in a culture apparatus and a culture method mounted on organ-on-a-chip or body-on-a-chip, high metabolic activity is required in a narrow space, and the cell culture apparatus and the cell culture method according to the above-described embodiment are superior to a cell culture apparatus and a cell culture method in the related art.

In addition, there is no technique for appropriately evaluating bile excretion in the in vitro culture technique for hepatocytes.

According to the cell culture apparatus and the cell culture method according to the above-described embodiment, it can be confirmed that expression of a transporter (MRP2) expressed on a membrane on a bile duct side of hepatocytes is improved, and it is possible to express functions that could not be realized by culture methods in the related art.

EXAMPLES

Examples 1 to 3

The cell culture apparatus 10 shown in FIG. 1 was produced. As the membrane 2, Transwell (pore diameter: 1 μm) with a thin Matrigel coat was used.

The thin Matrigel coat was formed by diluting Corning Matrigel Basement Membrane Matrix (Corning) with a serum-free medium and adding it to Transwell to be 100 μg/cm$^2$. This thin Matrigel coat was washed with PBS twice after being allowed to stand at room temperature for 1 hour or more.

As the cells 20, human hepatoma-derived cells HepG2, human vascular endothelial cells HUVEC, and human immortalized mesenchymal stem cells UCBTERT-21 were used in a composition shown in Table 1, and cultured in the cell culture apparatus 10.

In order to observe cells with fluorescence, HUVEC was subjected to fluorescent staining using Cell tracker Green (LifeTechnologies). HepG2 and UCBTERT-21 were subjected to fluorescent staining using Cell Tracker Red (LifeTechnologies). A culture solution was injected into each flow path of the cell culture apparatus 10 immediately before seeding the cells for air release. After cells (HepG2, HUVEC, and UCBTERT-21) were detached by a trypsin treatment, they were suspended in a medium (a culture solution), and counted.

The cells 20 were seeded by putting each cell suspension corresponding to the number of cells shown in Table 1 in a tube of 15-mL tube, collecting the cells by centrifugation, and then directly seeding the suspension resuspended in a medium (70 μL).

After seeding the cells 20, the cells were subjected to stationary culture for about 3 hours to make the cells sufficiently adhere to Transwell (the membrane 2). After that, a medium was further added to the well so that the total amount of medium was 1.15 mL. It was left for about 24 hours as it was, and circulating culture was started. The initial day of circulating culture was defined as Day 0 (0th culture day), and the circulating culture was performed while exchanging a medium of 1.15 mL every 1 to 3 days.

Sampling of a medium for albumin quantification was performed every 1 to 3 days, and at that time, medium exchange and observation with a phase contrast microscope were performed. Albumin quantification was performed by ELISA (using AssayPro, Albumin, Human, ELISA Kit, AssayMax). Localization of each cell in the cell aggregation was observed by a confocal laser microscope (Yokogawa Electric, CSU10).

Gene expression by quantitative PCR of each cell on 13th day after initial culture was analyzed. There are three types of genes to be analyzed: CYP1A2 and CYP3A4 of drug-metabolizing enzymes and albumin (Albumin). After each cell was washed with PBS twice, total RNA was extracted by RNeasy Plus Mini Kit (Qiagen). cDNA was prepared using QuantiTect Rev. Transcription Kit (Qiagen).

Quantitative PCR was performed using QuantiFast SYBR Green PCR Kit (Qiagen). As primers for individual genes, CYP1A2: Hs_CYP1A2_1_SG QuantiTect Primer Assay (Qiagen), CYP3A4: CYP3A4_1_SG QuantiTect Primer Assay (Qiagen), and Albumin: Hs_ALB_1_SG QuantiTect Primer Assay (Qiagen) were used, and as an internal standard, GAPDH: GAPDH_1_SG QuantiTect Primer Assay (Qiagen) was used. The result of quantitative PCR was normalized by the gene expression level of Day 0 according to a ratio of the number of cells.

CYP3A4 activity on 13th day after initial culture was measured using P450-Glo™ CYP3A4 Assay (Luciferin-IPA) (Promega). The amount of medium at the time of substrate addition was 1 mL, and after reaction was performed for 2 hours, luminescence was measured.

Figure 9:
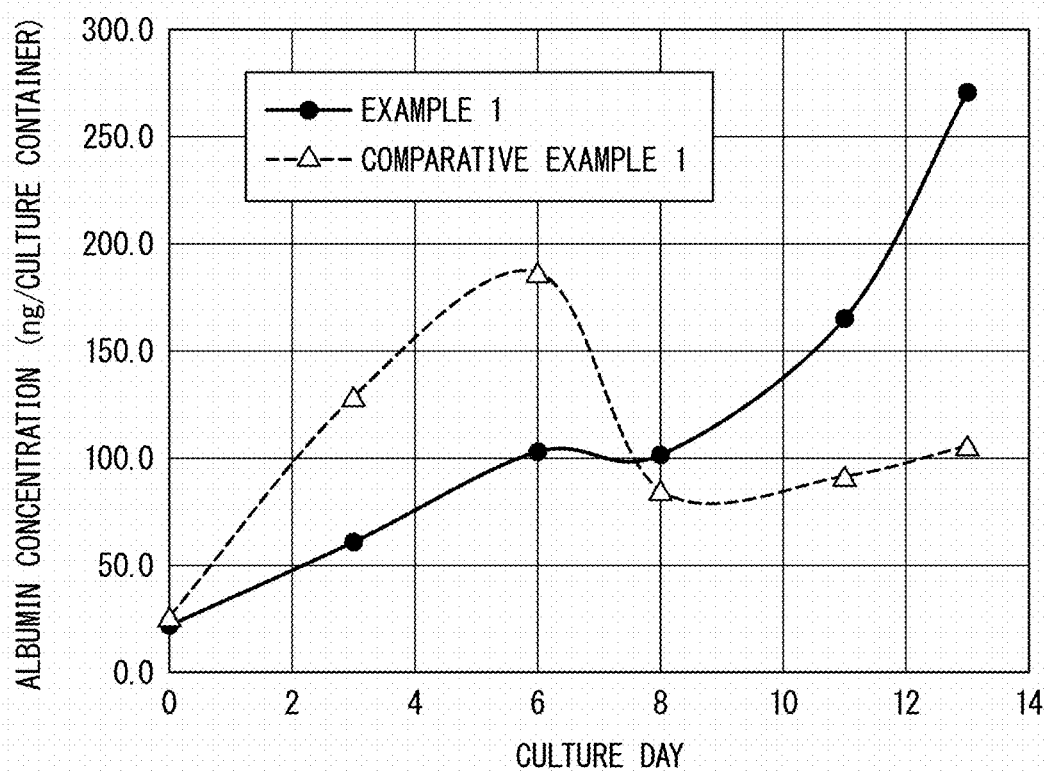
FIG. 9 is a graph showing change in albumin concentration in a culture solution.

FIG. 9 shows change in albumin concentration in the culture solution of Example 1.

Figure 10:
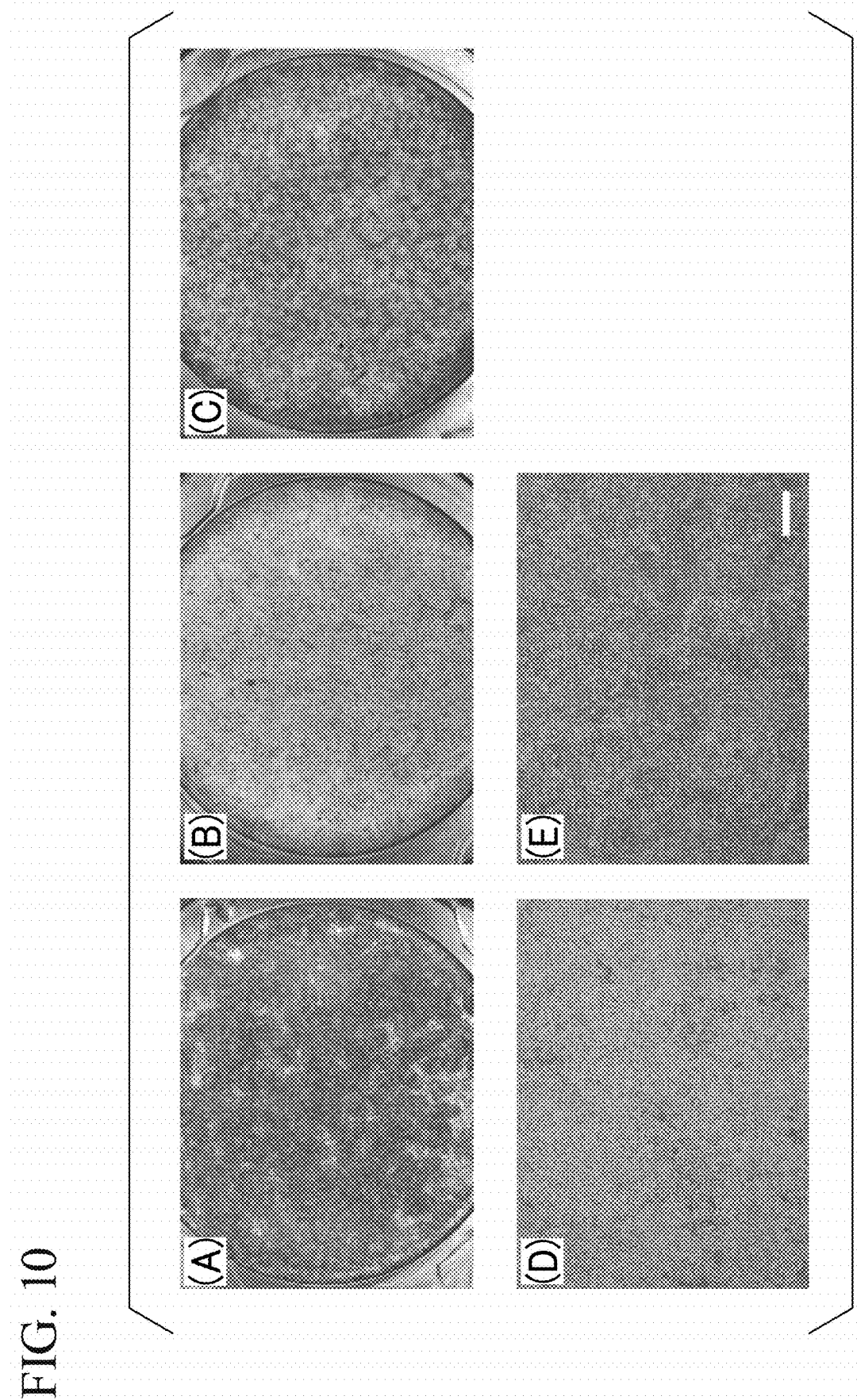
FIG. 10 shows phase-contrast observation images of cells.

FIGS. 10(A) to 10(C) show phase-contrast observation images (6th day after initial culture) of the cells in Examples 1 to 3, respectively.

Figure 11:
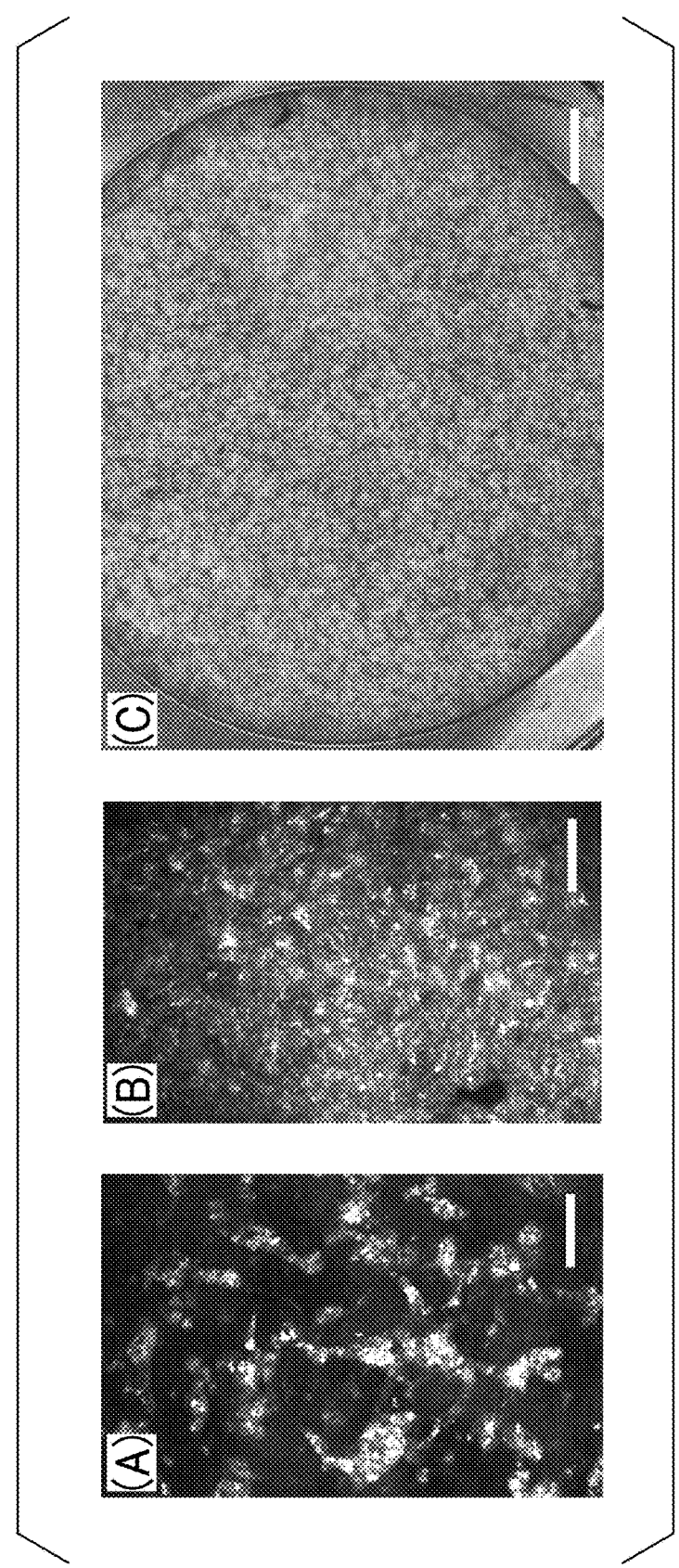
FIG. 11 shows observation images of cells with a confocal laser microscope and a phase-contrast observation image.

FIG. 11(A) shows an observation image of HUVEC with a confocal laser microscope in Example 3.

FIG. 11(B) shows an observation image of HepG2 and UCBTERT-21 with a confocal laser microscope in Example 3. FIG. 11(C) shows a phase-contrast observation image (5th day after initial culture) in Example 3.

Figure 12:
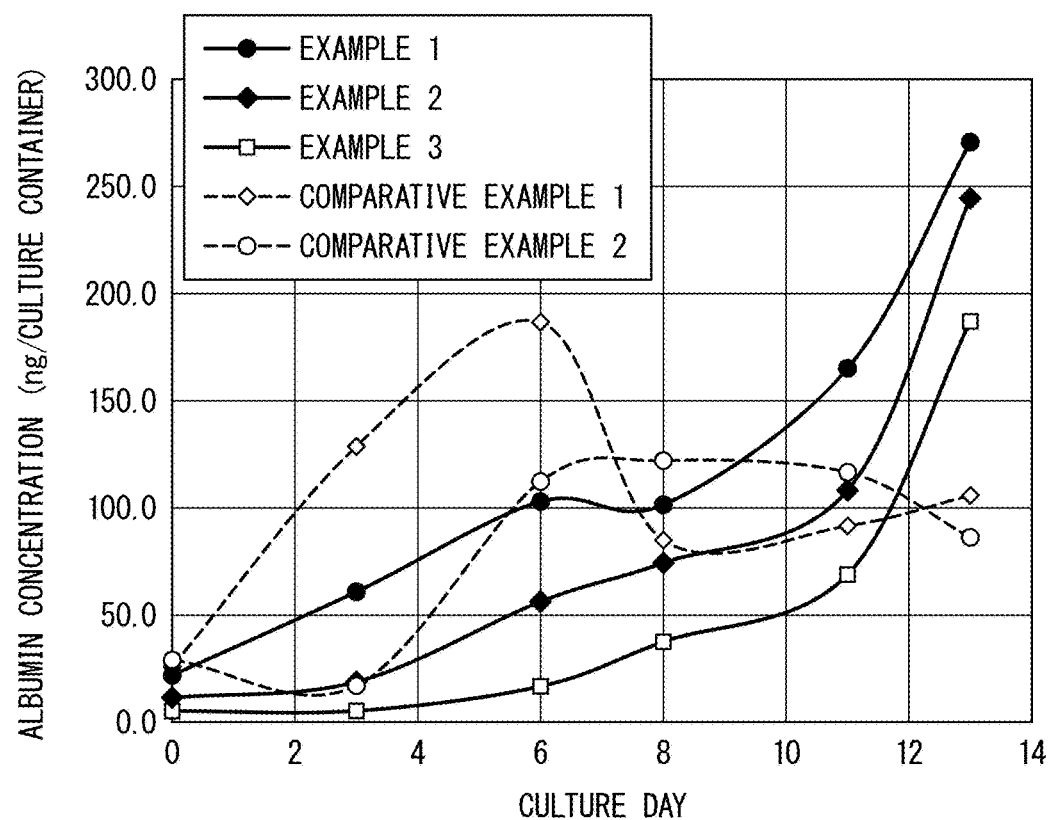
FIG. 12 is a graph showing change in albumin concentration in a culture solution.

FIG. 12 shows changes in albumin concentration in the culture solutions of Examples 1 to 3.

Figure 13:
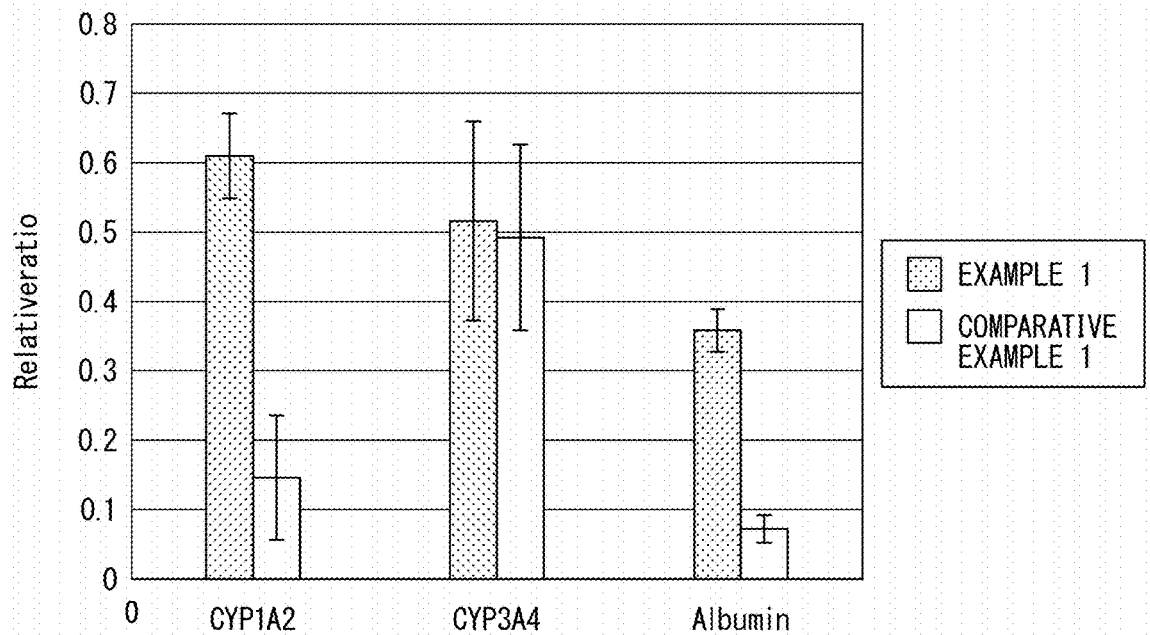
FIG. 13 is a graph showing gene expression related to the liver function.
Figure 14:
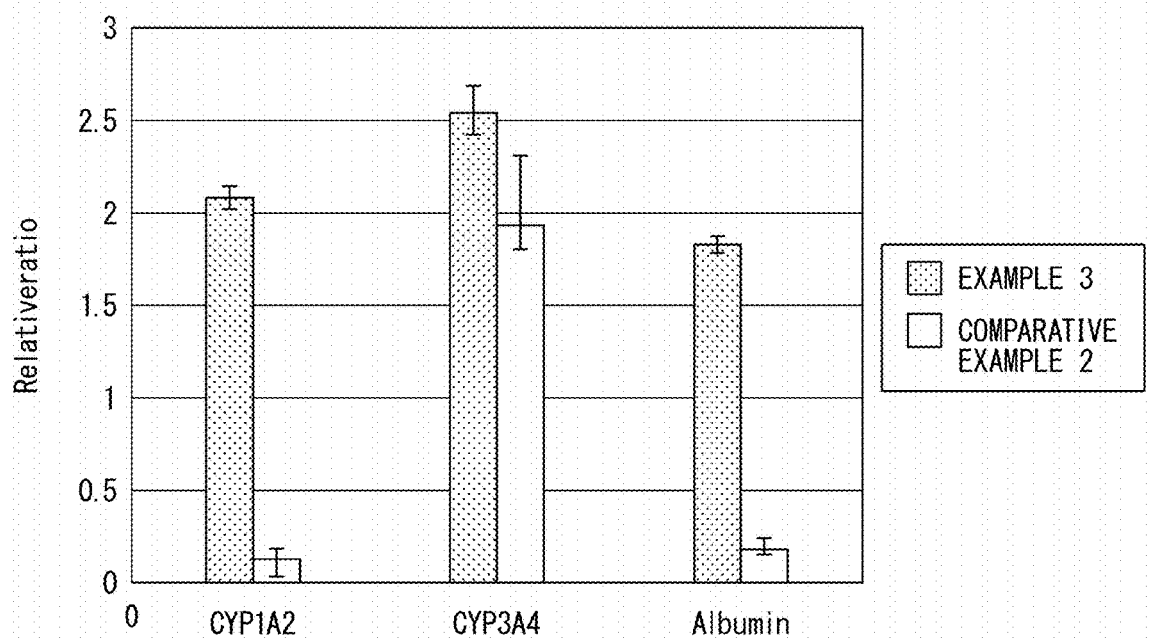
FIG. 14 is a graph showing gene expression related to the liver function.

FIG. 13 and FIG. 14 show gene expression related to the liver function in Example 1 and Example 3, respectively.

Figure 15:
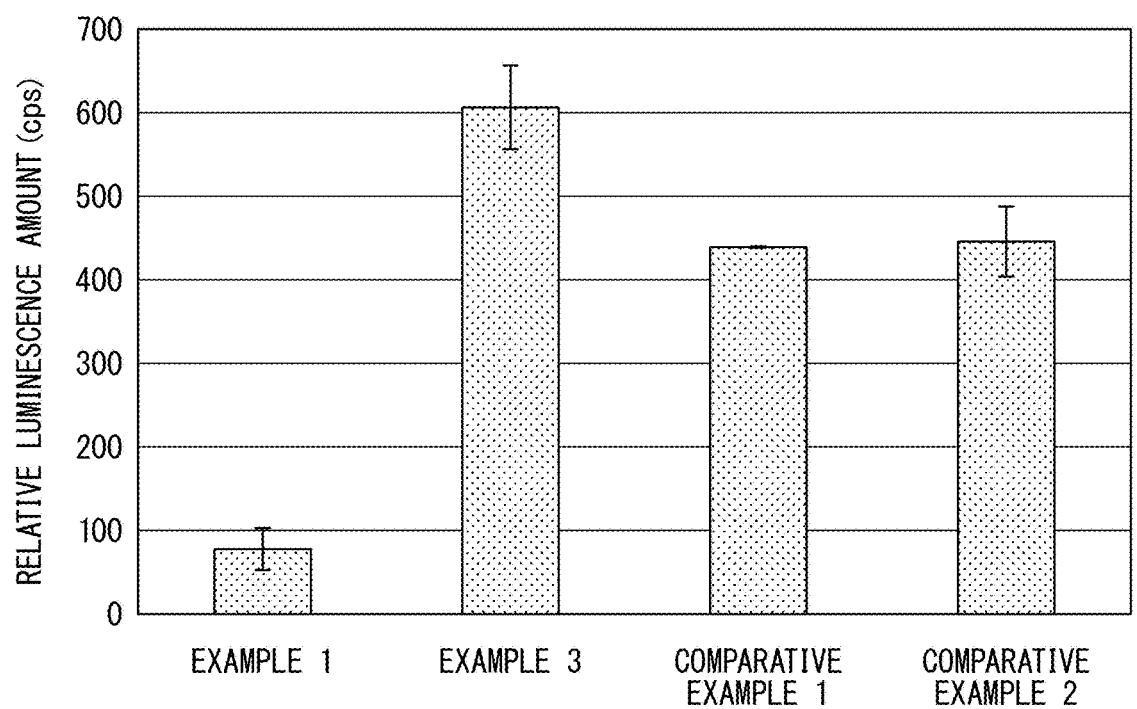
FIG. 15 is a graph showing a result of CYP3A4 activity measurement.

FIG. 15 shows results of CYP3A4 activity measurement in Example 1 and Example 3.

Comparative Examples 1 and 2

Using cells shown in Table 1, culture was performed using a dish having a diameter of 35 mm.

The cells were seeded by putting each cell suspension corresponding to the number of cells shown in Table 1 in a 15-mL tube, collecting the cells by centrifugation, and then directly seeding the suspension resuspended in a medium (2 mL).

FIGS. 10(D) to 10(E) show phase-contrast observation images (6th day after initial culture) of the cells in Comparative Examples 1 and 2, respectively.

TABLE 1

|  | HepG2 (cells) | HUVEC (cells) | UCBTERT-21 (cells) |
| --- | --- | --- | --- |
| Example 1 | $10 \times 10^4$ | — | — |
| Example 2 | $10 \times 10^4$ | $10 \times 10^4$ | $2.5 \times 10^4$ |
| Example 3 | $10 \times 10^4$ | $40 \times 10^4$ | $10 \times 10^4$ |
| Comparative Example 1 | $10 \times 10^4$ | — | — |
| Comparative Example 2 | $10 \times 10^4$ | $40 \times 10^4$ | $10 \times 10^4$ |

The medium was exchanged about 24 hours after seeding of the cells, and this day was defined as Day 0. Stationary culture was performed while exchanging a medium of 2 mL every 1 to 3 days.

Other conditions were the same as in Examples 1 to 3.

FIG. 9 shows change in albumin concentration in the culture solution of Comparative Example 1, and FIG. 12 shows changes in albumin concentration in the culture solutions of Comparative Examples 1 and 2.

FIG. 13 and FIG. 14 show gene expression related to the liver function in Comparative Example 1 and Comparative Example 2, respectively.

FIG. 15 shows results of CYP3A4 activity measurement in Comparative Example 1 and Comparative Example 2.

As shown in FIG. 9, in Example 1, the amount of produced albumin began to increase from around 8th day after initial culture, and the production amount continued to increase on 12th day. On the other hand, in Comparative Example 1, the amount of produced albumin reached a limit from around 8th day after initial culture. Therefore, it was found that from 8th day after initial culture, the amount of produced albumin in Example 1 using the cell culture apparatus 10 in FIG. 1 was higher than that in Comparative Example 1 in which culture was performed using a 35-mm dish that is a known culture container.

As shown in FIG. 10(C), in Example 3 in which HepG2 was co-cultured with HUVEC and UCBTERT-21 (the ratio of the number of cells was HepG2:HUVEC:UCBTERT-21=1:4:1), formation of a blood vessel-like network structure (a luminal structure) was confirmed.

As shown in FIG. 10(A), formation of a network structure was not confirmed under a condition not including HUVEC and UCBTERT-21 (Example 1; the ratio of the number of cells was 1:0:0).

As shown in FIG. 10(B), in Example 2 (the ratio of the number of cells was 1:1:0.25) in which the content of HUVEC and UCBTERT-21 was lower than that in Example 3, formation of a network structure was only partially confirmed.

As shown in FIG. 10(D) and FIG. 10(E), in Comparative Examples 1 and 2, formation of a blood vessel-like network structure was not confirmed regardless of the ratio of the number of cells.

As shown in FIG. 11(A), under a condition that fluorescent-stained HUVEC and UCBTERT-21 were co-cultured with HepG2 (the ratio of the number of cells was HepG2:HUVEC:UCBTERT-21=1:4:1), the same cell culture as in Example 3 was performed, and observation was performed on 5th day after initial culture using a confocal laser microscope. As a result, it was confirmed that HUVEC formed a network structure and a blood vessel-like tissue was formed.

As shown in FIG. 11(B), it was confirmed that two types of cell groups composed of HepG2 and UCBTERT-21 exist in the entire tissue.

As shown in FIG. 12, in Examples 2 and 3 in which HepG2 was co-cultured with HUVEC and UCBTERT-21 (the ratio of the number of cells was 1:1:0.25 and 1:4:1), the amount of produced albumin was slightly lower than that in Example 1 (the ratio of the number of cells was 1:0:0) using HepG2 alone.

However, in Examples 1 to 3, after long-term culture (for example, on 13th day after initial culture), the amount of produced albumin was larger than that in Comparative Examples 1 and 2.

On the other hand, as shown in FIG. 13 and FIG. 14, expression of CYP1A2 gene and Albumin gene of each of Example 1 and Example 3 was increased as compared with Comparative Example 1 and Comparative Example 2. Further, as shown in FIG. 15, activity of CYP3A4 in Example 3 was increased as compared with Example 1, Comparative Example 1, and Comparative Example 2.

Example 4, and Comparative Examples 3 and 4

The following shows results of comparison of the number of cells per area between a cell culture apparatus of Example 4 corresponding to an example of the cell culture apparatus according to the above-described embodiment and a cell culture container according to Comparative Examples 3 and 4 corresponding to a general cell culture container.

In Example 4, similarly to Examples 1 to 3 described above, the cell culture apparatus 10 shown in FIG. 1 was produced, and cells were seeded as shown in Table 2 below.

Similarly to Comparative Examples 1 and 2, as Comparative Example 3, a 35-mm dish that is a cell culture container generally used was prepared, and cells were seeded as shown in Table 2 below.

Further, as Comparative Example 4, a 96-well plate as a general cell culture container was prepared, and cells were seeded as shown in Table 2 below.

TABLE 2

|  | Example 4 | Comparative Example 3 | Comparative Example 4 |
|---|---|---|---|
| Culture area/well | 0.143 cm$^2$ | 9.6 cm$^2$ | 0.32 cm$^2$ |
| Amount of medium/culture container | 1 mL | 1 mL | 100 μL |
| Number of HepG2 cells/culture container | $10 \times 10^4$ cells | $10 \times 10^4$ cells | $0.36 \times 10^4$ cells |
| Number of cells/culture area | $80 \times 10^4$ cells/cm$^2$ | $1.0 \times 10^4$ cells/cm$^2$ | $1.0 \times 10^4$ cells/cm$^2$ |

As shown in Table 2, as compared with a culture method in the related art such as Comparative Examples 3 and 4, in Example 4, it was possible to introduce about 80 times cells per area into a culture container and culture.

As described above, according to the cell culture apparatus of Example 4, it was possible to culture a large amount of cells while maintaining expression of metabolic enzymes and the like, even under a condition that a culture area was small.

Examples 5 to 8

Similarly to Example 1, the cell culture apparatus 10 shown in FIG. 1 was produced.

Seeding of the cells 20 in Examples 5 to 8 was performed by putting each cell suspension adjusted to correspond to the number of cells shown in Table 3 in a 15-mL tube, collecting the cells by centrifugation, and then directly seeding the suspension resuspended in a medium (60 to 80 μL).

After seeding the cells 20, the cells were subjected to stationary culture for about 3 hours to make the cells sufficiently adhere to Transwell (the membrane 2). After that, a medium was further added to the well so that the total amount of medium was 1.15 mL.

It was left for about 24 hours as it was, and circulating culture was started. The initial day of circulating culture was defined as Day 0 (0th culture day), and the circulating culture was performed while exchanging a medium of 1.15 mL every 2 to 3 days.

As shown in Table 4, a flow rate of a medium was measured on Day 1 (1st day after initial culture), Day 3 (3rd day after initial culture), and Day 15 (15th day after initial culture), and the cell aggregation was fixed on Day 16 (16th day after initial culture) with 4% of paraformaldehyde.

Using the produced section, fluorescent immunostaining was performed using an anti-CD31 (PECAM-1) antibody that stains a cell membrane of HUVEC and an anti-MRP2 (ABCC2) antibody that stains a bile duct side membrane of the liver.

TABLE 3

| | Cell number ratio | HepG2 (cells) | HUVEC (cells) | UCBTERT-21 (cells) |
|---|---|---|---|---|
| Example 5 | 1:0:0 | $10 \times 10^4$ | | |
| Example 6 | 6:0:0 | $60 \times 10^4$ | | |
| Example 7 | 1:1:0.25 | $10 \times 10^4$ | $10 \times 10^4$ | $0.25 \times 10^4$ |
| Example 8 | 1:4:1 | $10 \times 10^4$ | $40 \times 10^4$ | $10 \times 10^4$ |

TABLE 4

| | Cell number ratio | Day 1 | Day 3 | Day 15 |
|---|---|---|---|---|
| Example 5 | 1:0:0 | 8.9 μL/min | 11.4 μL/min | 7.6 μL/min |
| Example 6 | 6:0:0 | 2.6 μL/min | 3.3 μL/min | Occlusion |
| Example 7 | 1:1:0.25 | 3.4 μL/min | 11.1 μL/min | 3.2 μL/min |
| Example 8 | 1:4:1 | 3.9 μL/min | 5.9 μL/min | 2.0 μL/min |

Table 4 shows the results of a medium flow rate under each culture condition.

As shown in Table 4, in all of Examples 5 to 8, Day 3 had the highest medium flow rate, and on 15th day after initial culture in which increase in amount of produced albumin or enzyme activity was observed, a tendency that the medium flow rate decreased under all conditions was observed.

The fact that the medium flow rate increases with tissue maturation as in the results up to Day 3 is considered to be an advantage of pressure drive circulating culture.

On 15th day after initial culture, in Example 6 (6:0:0) in which cells having 6 times the number of cells in Example 5 were seeded, medium circulation could not be confirmed.

It is considered that this result was caused by the fact that grown HepG2 flowed into a flow path and clogged the flow path.

In addition, it was shown that a medium in a culture container makes one cycle in 1.7 to 9.6 hours.

Figure 16:
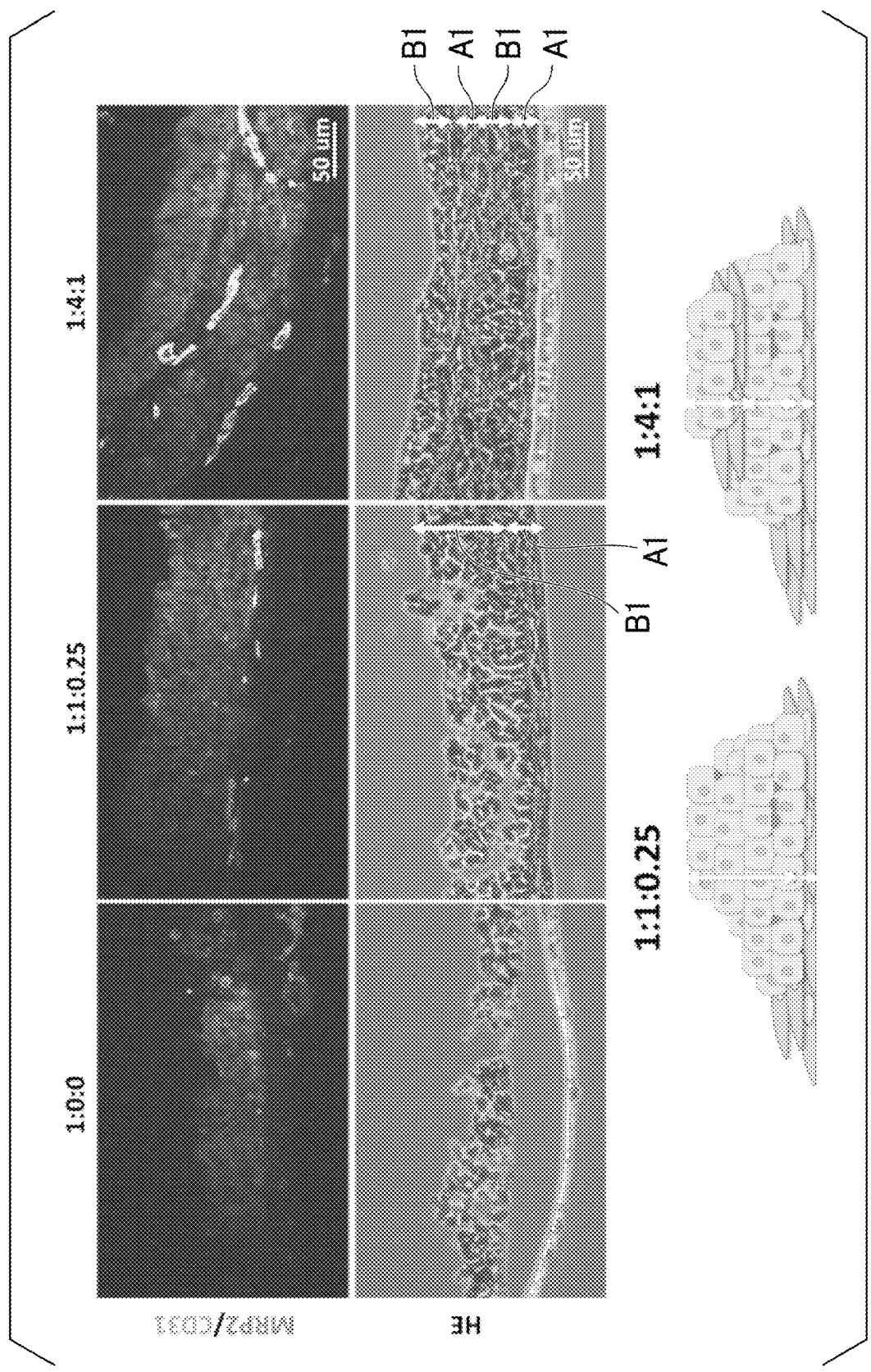
FIG. 16 is a schematic view of immunostaining, an HE staining image, and cells having a three-dimensional structure in each seeding condition.

FIG. 16 shows a schematic view of results of immunostaining (MRP2/CD31) of cells, results of HE staining (hematoxylin and eosin staining), and cells having a three-dimensional structure.

The results of Example 6 (6:0:0) were not shown because the results were almost the same as those in Example 5 (1:0:0) in that cell death progressed and the tissue was brittle.

As shown in Example 5 and Example 6, in HepG2 alone, a difference between a relatively dense part and a sparse part of the cell mass structure was large, and a signal of MRP2 could hardly be observed.

As shown in FIG. 16, in Example 7 (1:1:0.25) and Example 8 (1:4:1) in which HepG2, HUVEC, and UCB-TERT-21 were co-cultured, a large amount of expression of MRP2 was observed in a portion where HepG2s were considered to be adjacent with each other.

That is, expression of MRP2, which is a transporter expressed on a membrane on a bile duct side of hepatocytes, was enhanced in co-culture of vascular endothelial cells such as HUVEC and mesenchymal stem cells such as UCBTERT-21, and results were confirmed that co-culture of vascular endothelial cells and mesenchymal stem cells was expected to improve the bile excretory function.

When comparing two conditions of Example 7 and Example 8 in which co-culture was performed, tissue formation with a more uniform cell density occurred in Example 8 (1:4:1), but there was no clear difference in expression of MRP2 between Example 7 and Example 8.

As shown in FIG. 16, in Example 7 and Example 8, HUVECs aggregated in a sheet shape in parallel with a porous membrane (location indicated by an arrow A1 in the schematic view of FIG. 16), and lamination (location indicated by an arrow B1 in the schematic view of FIG. 16) of HepG2 was observed on HUVEC.

Further, as shown in Example 8 (a condition of 1:4:1), when the amount of HUVEC was increased, the HUVEC sheet became two layers (see locations of arrows A1 and B1 in the schematic view of FIG. 16).

NPL 8 discloses a method of performing perfusion culture of a three-dimensional tissue by using a built-in peristaltic pump for liquid feeding.

On the other hand, in the cell culture apparatus and the cell culture method according to the above-described embodiment of the present invention, a configuration is provided in which a culture solution is circulated by repeating pressurization and release of atmospheric pressure via vent holes installed in a culture chamber and a culture solution storage chamber.

In general, in a case of using a built-in peristaltic pump for liquid feeding, cell culture is performed under a flow condition of a constant flow rate regardless of a structure in the three-dimensional tissue. In this case, when vascular tissue is not developed in the three-dimensional tissue, an excessive liquid-feeding load is applied to the cell tissue.

On the other hand, in a liquid-feeding method by pressure drive according to the above-described embodiment, since a liquid is fed while being pressurized at a constant pressure, a flow rate of a liquid such as a medium is adjusted according to development of the vascular tissue in the three-dimensional tissue.

In practice, as shown in Table 4, in Examples 5 to 8, increase in the medium flow rate in accordance with development of the vascular tissue and liver tissue was observed from Day 1 to Day 3.

Further, as in Examples 7 and 8, in a culture system containing vascular endothelial cells such as HUVEC, a tendency of adjusting a flow rate of a liquid such as a medium was remarkable according to development of the vascular tissue in the three-dimensional tissue.

In Examples 5 to 8, decrease in flow rate and occlusion due to growth of hepatocytes were confirmed from Day 3 to Day 15, but it is considered that decrease in flow rate and occlusion can be solved by using a culture solution capable of maintaining the vascular tissue for a long time.

In order to maintain the vascular tissue for a long time, for example, a method of adding a growth factor such as VEGF which is a vascular endothelial cells growth factor to a culture solution can be considered.

According to the cell culture apparatus and the cell culture method according to the present embodiment, hepatocytes and vascular endothelial cells can be co-cultured under perfusion conditions, and a three-dimensional tissue of hepatocytes having a blood vessel-like structure can be constructed and cultured.

Accordingly, as shown in Table 2, as compared with a culture method in the related art, in the cell culture apparatus and the cell culture method according to the present embodiment, for example, it was possible to introduce about 80 times more cells per area into a culture container and culture.

That is, according to the present embodiment, it can be expected that a large amount of cells can be cultured even in a small culture area while maintaining expression of metabolic enzymes and the like.

In general, in a culture system mounted on organ-on-a-chip or body-on-a-chip, high metabolic activity is required in a narrow space, and the cell culture apparatus and the cell culture method according to the present embodiment are superior to a culture method in the related art.

In addition, a technique for appropriately evaluating bile excretion in the in vitro culture technique for hepatocytes is not confirmed at present.

According to the cell culture apparatus and the cell culture method according to the present embodiment, as shown in Examples 7 and 8, it is confirmed that expression of a transporter (MRP2) expressed on a membrane on a bile duct side of hepatocytes is improved, and it is considered that functions that cannot be realized by culture methods in the related art can be expressed.

Each configuration and the combination thereof in the present embodiment described above are merely examples, and addition, omission, replacement, and other changes of the configuration are possible without departing from the spirit of the present invention. The present invention is not limited by each embodiment, but is limited only by the scope of the claims.

The cell culture apparatus 10 shown in FIG. 1 may have the configuration including the storage tank 11, the first pressure-adjusting unit 14A, and the second pressure-adjusting unit 14B.

Although the storage tank 11 of the cell culture apparatus 10 shown in FIG. 1 has the tank main body 12 and the lid portion 13, the storage tank 11 is not limited to the configuration in which the tank main body 12 and the lid portion 13 are separately provided, and the storage tank in which the tank main body and the lid portion are integrated may be employed.

The cell culture apparatus according to the present embodiment may include the first pressure-adjusting unit that adjusts the pressure in the culture chamber and the second pressure-adjusting unit that adjusts the pressure in the culture solution storage chamber.

In the cell culture apparatus according to the present embodiment, the structure for adjusting the pressure in the culture chamber and the culture solution storage chamber is not particularly limited. For example, a structure for increasing the pressure in the inner surface-side space (or the culture solution storage chamber) of the culture chamber by supplying the culture solution may be adopted, or a structure for decreasing the pressure in the outer surface-side space (or the culture solution storage chamber) of the culture chamber by discharging part of the culture solution in the inner surface-side space (or the culture solution storage chamber) of the culture chamber may be adopted. Further, a structure for changing the pressure by changing the volumes of the culture chamber and the culture solution storage chamber may be adopted.

Cells to be cultured in the present embodiment are not particularly limited, and for example, cells derived from animals including humans, cells derived from plants, cells derived from microorganisms, and the like can be used according to the purpose.

The present embodiment is useful in the field of cell engineering, the field of regenerative medicine, the field of biotechnology, the field of tissue engineering, and the like. It is particularly useful for development of pharmaceutical drugs and basic research in cell biology.

REFERENCE SIGNS LIST

1: culture chamber
1a: inner surface-side space
1b: outer surface-side space
2: membrane
3: culture solution storage chamber
4: culture solution introduction flow path
5: culture solution discharge flow path
6: bypass flow path (bypass path)
6a: resistance flow path part
9, 9A: cell culture unit
10, 10a, 10b, 10A, 10B: cell culture apparatus
11, 11A: storage tank
51, 52: check valve (backflow prevention mechanism)
53, 54, 117: Laplace valve (backflow prevention mechanism)
C: culture solution

The invention claimed is:

1. A cell culture apparatus, comprising:
a storage tank including one or a plurality of cell culture units,
wherein the cell culture unit includes
a culture chamber having an inner surface-side space in which a culture solution is stored,
a permeable membrane having a first surface to which cells are adherable and a second surface opposite to the first surface, the first surface facing the inner surface-side space,
a culture solution storage chamber that stores the culture solution,
a culture solution introduction flow path that introduces the culture solution in the culture solution storage chamber to the inner surface-side space, wherein the culture solution introduction flow path is connected at a first end to the culture solution storage chamber and at a second end to the culture chamber inner surface-side space,
a culture solution discharge flow path that sends, to the culture solution storage chamber, the culture solution which permeates through the membrane from the inner surface-side space and flows into an outer surface-side space that the second surface of the membrane faces, wherein the culture solution discharge flow path is connected at a first end to the culture chamber outer surface-side space and at a second end to the culture solution storage chamber, and
a bypass flow path that introduces the culture solution in the inner surface-side space to the culture solution discharge flow path without passing through the membrane, wherein the bypass flow path is connected at a bottom portion of the culture chamber and at the culture solution discharge flow path.

2. The cell culture apparatus according to claim 1, further comprising:
a backflow prevention mechanism that regulates a flow of the culture solution reverse to a circulation flow of the culture solution returning back to the culture solution storage chamber from the culture solution storage chamber via the inner surface-side space and the outer surface-side space.

3. The cell culture apparatus according to claim 2, wherein the backflow prevention mechanism is provided in the culture solution introduction flow path.

4. The cell culture apparatus according to claim 2, wherein the backflow prevention mechanism is a Laplace valve that prevents a gas flow in a direction reverse to the circulation flow,
the Laplace valve is provided in the culture solution introduction flow path, and
an extension pipeline connected to the culture solution introduction flow path is provided in the culture chamber.

5. The cell culture apparatus according to claim 1, wherein the bypass flow path has a resistance flow path part of which a flow path sectional area is $1/10$ or less of that of the other part in the bypass flow path.

6. The cell culture apparatus according to any claim 1, wherein the storage tank has the plurality of cell culture units, and
at least two of the culture chambers in the plurality of cell culture units or at least two of second culture solution storage chambers in the plurality of cell culture units communicate with each other so that gas is allowed to flow therethrough.

7. The cell culture apparatus according to claim 1, wherein the culture chamber and the culture solution storage chamber have vent holes through which gas is supplied to and discharged from the culture chamber and the culture solution storage chamber.

8. The cell culture apparatus according to claim 1, wherein the storage tank includes:
the plurality of cell culture units, and
a gas flow path that allows the plurality of cell culture units to communicate with each other,
the gas flow path is configured to circulate the culture solution between the plurality of cell culture units by simultaneously pressurizing insides of the plurality of cell culture units, and
the gas flow path is connected between at least two of the culture chambers of the plurality of cell culture units.

* * * * *